United States Patent
Gentner

(10) Patent No.: US 11,125,732 B2
(45) Date of Patent: Sep. 21, 2021

(54) SYSTEM, APPARATUS, AND METHOD FOR MONITORING ORGANIC COMPOUNDS IN A GAS ENVIRONMENT

(71) Applicant: YALE UNIVERSITY, New Haven, CT (US)

(72) Inventor: Drew Gentner, New York, NM (US)

(73) Assignee: Yale University, New Haven, CT (US)

( * ) Notice: Subject to any disclaimer, the term of this patent is extended or adjusted under 35 U.S.C. 154(b) by 55 days.

(21) Appl. No.: 16/080,753

(22) PCT Filed: Apr. 14, 2017

(86) PCT No.: PCT/US2017/027523
§ 371 (c)(1),
(2) Date: Aug. 29, 2018

(87) PCT Pub. No.: WO2017/180933
PCT Pub. Date: Oct. 19, 2017

(65) Prior Publication Data
US 2019/0094195 A1    Mar. 28, 2019

Related U.S. Application Data

(60) Provisional application No. 62/322,980, filed on Apr. 15, 2016.

(51) Int. Cl.
*G01N 1/00*        (2006.01)
*G01N 30/08*       (2006.01)
(Continued)

(52) U.S. Cl.
CPC ........... *G01N 33/0047* (2013.01); *G01N 1/00* (2013.01); *G01N 30/08* (2013.01); *G01N 30/12* (2013.01);
(Continued)

(58) Field of Classification Search
CPC .......... G01N 1/405; G01N 2001/4088; G01N 2030/025; G01N 2030/084;
(Continued)

(56) References Cited

U.S. PATENT DOCUMENTS 4,301,114 A * 11/1981 Rounbehler ........... B01D 53/02
422/52
5,342,786 A   8/1994 Capuano
(Continued)

FOREIGN PATENT DOCUMENTS

CN    101135668 A    3/2008
CN    101393222 A    3/2009
(Continued)

OTHER PUBLICATIONS

Extended European Search Report for Application No. EP17783177.3, dated Jan. 8, 2020, 9 pages.
(Continued)

*Primary Examiner* — Natalie Huls
(74) *Attorney, Agent, or Firm* — Riverside Law LLP

(57) ABSTRACT

The invention relates to a system and micro monitor apparatus, a space-, time-, and cost-efficient device to concentrate, identify, and quantify organic compounds in gas environments. The invention further relates to a method centered on gas chromatography for identifying and quantifying organic compounds in gas environments, using air as the carrier gas, without the need for a compressed pre-bottled purified carrier gas.

13 Claims, 30 Drawing Sheets

(51) Int. Cl.
*G01N 30/88* (2006.01)
*G01N 1/40* (2006.01)
*G01N 30/02* (2006.01)
*G01N 30/64* (2006.01)
*G01N 33/00* (2006.01)
*G01N 30/12* (2006.01)
*G01N 30/20* (2006.01)
*G01N 30/30* (2006.01)
*G01N 30/32* (2006.01)

(52) U.S. Cl.
CPC .............. *G01N 30/20* (2013.01); *G01N 30/30* (2013.01); *G01N 30/32* (2013.01); *G01N 30/64* (2013.01); *G01N 30/88* (2013.01); *G01N 33/0006* (2013.01); *G01N 33/0073* (2013.01); *G01N 1/405* (2013.01); *G01N 2001/4088* (2013.01); *G01N 2030/025* (2013.01); *G01N 2030/085* (2013.01); *G01N 2030/121* (2013.01); *G01N 2030/3084* (2013.01); *G01N 2030/326* (2013.01); *G01N 2030/642* (2013.01); *G01N 2030/884* (2013.01); *G01N 2033/0019* (2013.01)

(58) Field of Classification Search
CPC ..... G01N 2030/884; G01N 2033/0019; G01N 30/08; G01N 30/0047; G01N 30/88; G01N 30/6095
See application file for complete search history.

(56) References Cited

U.S. PATENT DOCUMENTS

| | | | | |
|---|---|---|---|---|
| 6,258,263 | B1* | 7/2001 | Henderson | G01N 30/6043 204/451 |
| 6,306,200 | B1* | 10/2001 | Yu | G01N 30/466 73/23.36 |
| 6,460,401 | B1 | 10/2002 | Hoshino | |
| 6,497,138 | B1* | 12/2002 | Abdel-Rahman | G01N 30/466 73/23.26 |
| 8,230,719 | B2 | 7/2012 | Fisher | |
| 8,277,544 | B2* | 10/2012 | Guan | G01N 30/465 96/101 |
| 8,347,688 | B2 | 1/2013 | O'Brien | |
| 8,999,245 | B2* | 4/2015 | Wang | G01N 30/461 422/89 |
| 10,201,644 | B2* | 2/2019 | Haggstrom | A61M 1/0027 |
| 2003/0233862 | A1* | 12/2003 | Wise | G01N 30/60 73/23.39 |
| 2005/0063865 | A1* | 3/2005 | Bonne | G01N 30/6039 422/68.1 |
| 2005/0085740 | A1* | 4/2005 | Davis | G01N 27/624 600/532 |
| 2007/0000838 | A1* | 1/2007 | Shih | G01N 30/466 210/656 |
| 2007/0029477 | A1* | 2/2007 | Miller | G01N 30/7206 250/290 |
| 2007/0164231 | A1 | 7/2007 | Truche | |
| 2008/0092626 | A1* | 4/2008 | Lehmann | G01N 30/56 73/23.3 |
| 2008/0121016 | A1* | 5/2008 | Shah | G01N 30/88 73/23.42 |
| 2008/0264491 | A1* | 10/2008 | Klee | B01L 3/567 137/9 |
| 2008/0300501 | A1* | 12/2008 | Willard | G01N 27/4143 600/532 |
| 2011/0113866 | A1* | 5/2011 | Finlay | G01N 30/6095 73/61.52 |
| 2011/0143952 | A1* | 6/2011 | Lewis | G01N 30/6095 506/8 |
| 2012/0118144 | A1* | 5/2012 | Cates | G01N 30/24 95/19 |
| 2015/0153299 | A1* | 6/2015 | Chou | G01N 33/0075 205/775 |
| 2017/0074857 | A1* | 3/2017 | Dennis | A61B 5/4833 |

FOREIGN PATENT DOCUMENTS

| | | |
|---|---|---|
| CN | 102498381 A | 6/2012 |
| CN | 102549440 A | 7/2012 |
| CN | 103376293 A | 10/2013 |
| CN | 103884768 A | 6/2014 |
| JP | 2003521688 A | 7/2003 |
| JP | 2006515673 A | 6/2006 |
| JP | 2010537190 A | 12/2010 |
| KR | 20090019717 A | 2/2009 |
| WO | 0155714 A1 | 8/2001 |
| WO | 2004038400 A2 | 5/2004 |
| WO | 2009025488 A2 | 2/2009 |
| WO | 2015134390 A | 9/2015 |

OTHER PUBLICATIONS

Tzeng Te-Hsuen et al.: "A Portable Micro Gas Chromatography System for Lung Cancer Associated Volatile Organic Compound Detection", IEEE Journal of Solid-State Circuits, IEEE Service Center, Piscataway, NJ, USA, vol. 51, No. 1, Jan. 1, 2016 (Jan. 1, 2016), pp. 259-272, XP011596423, ISSN: 0018-9200, DOI: 10.1109/JSSC.2015.2489839 [retrieved on Dec. 30, 2015].
Chinese Office Action (with English language translation) for App. No. CN201780016644.1, dated Sep. 17, 2020, 15 pages.
Indian Examination Report for App. No. 201817035614, dated Mar. 22, 2021, 9 pages.
Japanese Office Action (with English translation) for App. No. JP2018-553906, dated Mar. 2, 2021, 14 pages.
Korean Office Action (including English translation) for App. No. KR10-2018-7032866, dated Jul. 13, 2021, 10 pages.

* cited by examiner

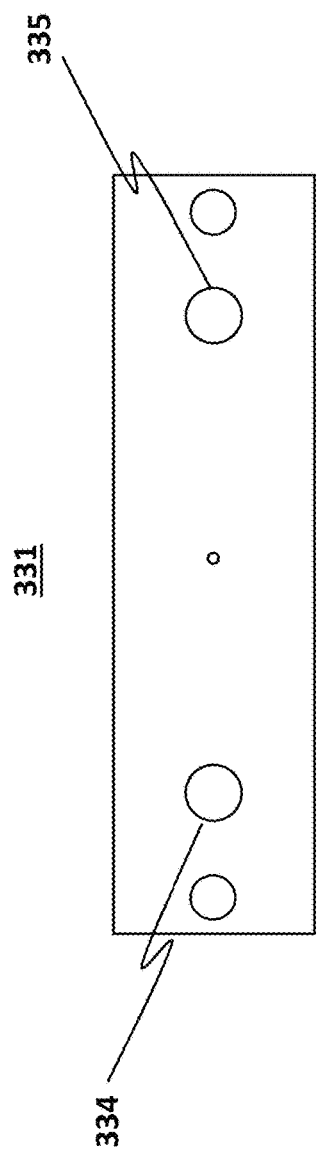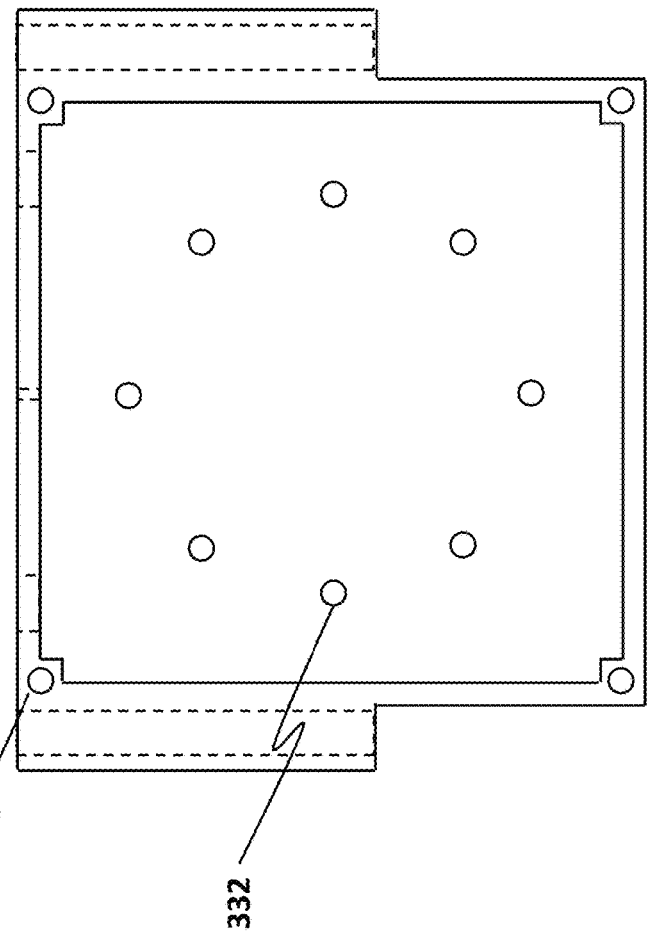

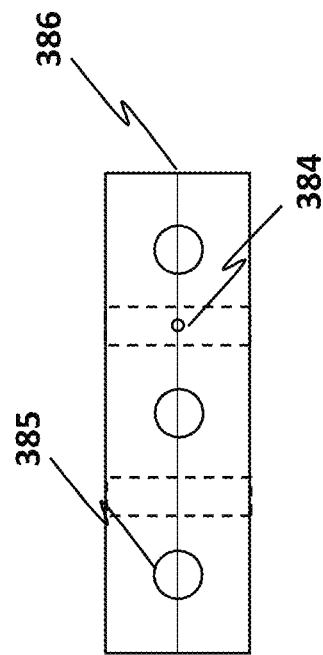
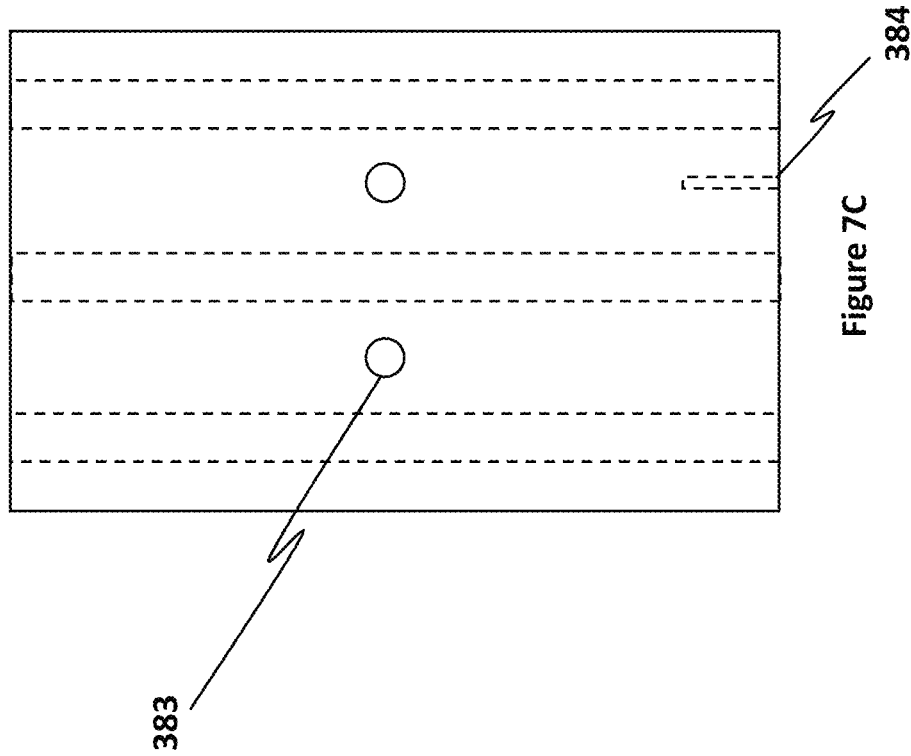
Figure 7C
Figure 7D

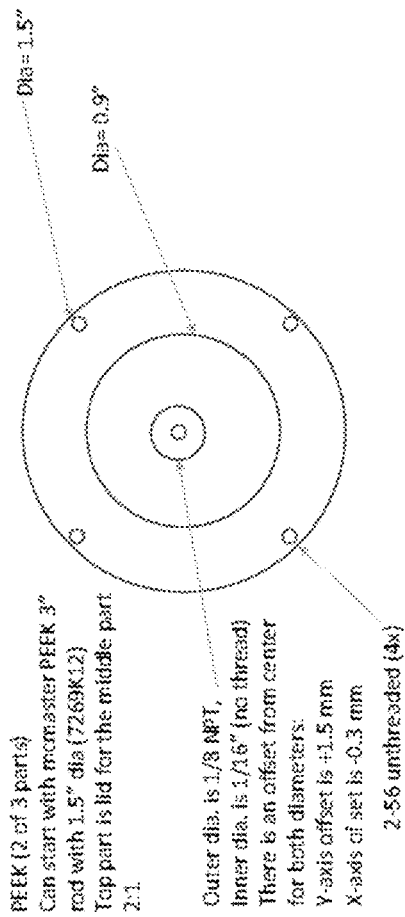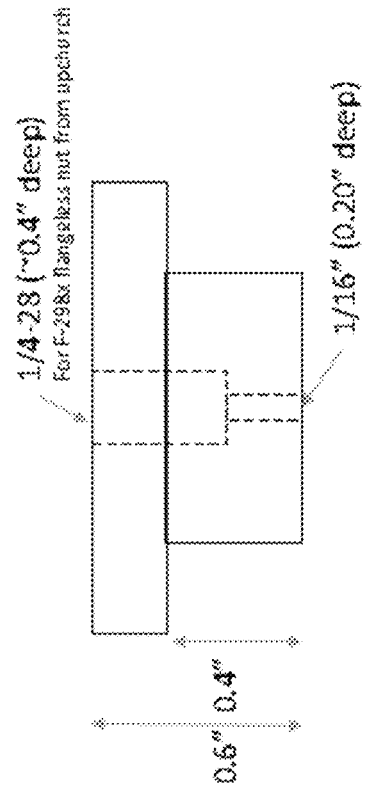
Figure 8A
Figure 8B
Figure 8

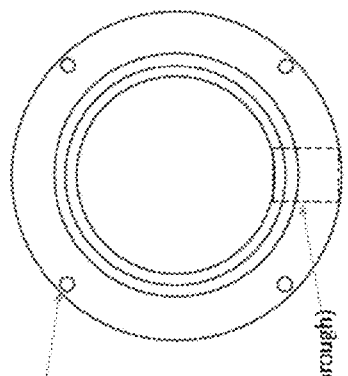
Figure 9A
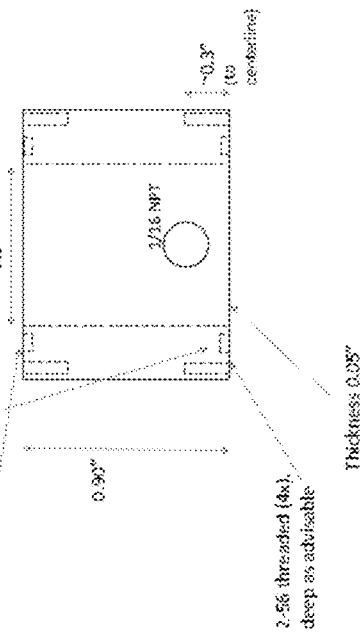
Figure 9B
Figure 9

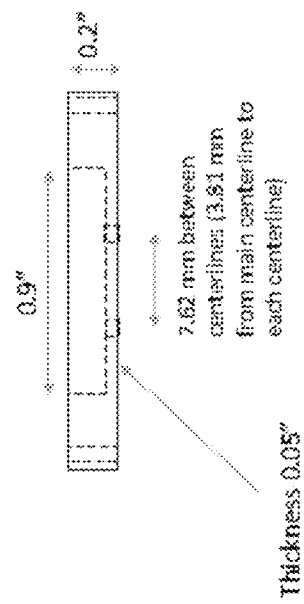
Figure 10B
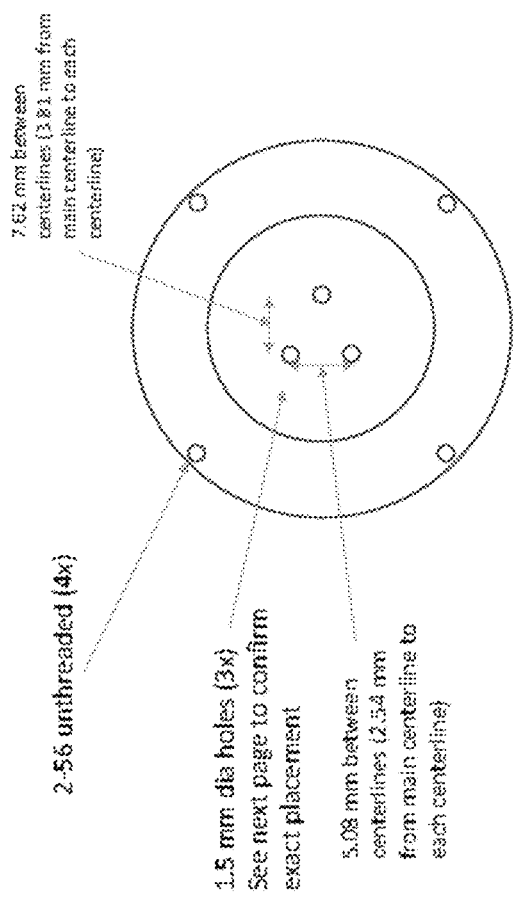
Figure 10A
Figure 10

SYSTEM, APPARATUS, AND METHOD FOR MONITORING ORGANIC COMPOUNDS IN A GAS ENVIRONMENT

CROSS-REFERENCE TO RELATED APPLICATIONS

This application is a national stage entry of PCT/US17/27523, filed Apr. 14, 2017, which claims priority to U.S. Provisional application No. 62/322,980 filed on Apr. 15, 2016, both of which are incorporated herein by reference in their entireties.

BACKGROUND OF THE INVENTION

In general, the measurements of organic compounds, including volatile organic compounds (VOCs) in the atmosphere or other environments, require instrumentation that is large (smallest is ~2 ft.×2 ft.×2 ft.), expensive (range $25k-500k), and requires consumable gases for chromatography, e.g., high purity helium, hydrogen, and/or nitrogen cylinders. Science progress, health screening, environmental monitoring, and regulatory policy is greatly limited by these restrictions and their costs, even more so in the developing world or disadvantaged communities. Current measurement tools either require the installation (and operation by a trained expert) of large gas chromatographs and/or mass spectrometers at field locations, or it requires the capture of air samples in 1 ft. gas canisters that are then transported (even cross-oceanic distances) to be analyzed in a lab, and those measurements are limited by what can be recovered from the canister due to condensation and adsorption to its walls.

Occupational and industrial settings have to rely on adsorbent "tubes" or "badges" or chemically nonselective sensors that provide limited daily, or longer, average measurements, or data of poor accuracy and selectivity, respectively. Tools for human health screening are very expensive and may require tests that are either intrusive or involve radiation, so the field of human breath, or other gaseous media, analysis shows great promise for its potential as a low-cost, non-intrusive method. However, available methods for breath analysis are extremely expensive and rare given the specialized expertise needed for upkeep and operation, e.g., real-time atmospheric pressure ionization mass spectrometers. The problem requires a robust, low-cost solution that can be dispersed across health care service networks.

Thus, there is a continuing need in the art for systems and methods for identifying and quantifying organic compounds in gas environments, in particular systems and methods which operate without the need for a compressed carrier gas. The present invention addresses this continuing need in the art.

SUMMARY OF INVENTION

In one aspect, the invention relates to a system for analyzing a gas mixture, comprising: a filter; a trap; a chromatographic column; a detector; and a pump, wherein the trap and the pump are fluidly connected to form a first gas flow path, and wherein the filter, the trap, the chromatographic column, the detector, and the pump, are fluidly connected to form a second gas flow path. In one embodiment, the detector and the pump are fluidly connected to form a third gas flow path. In another embodiment, the chromatographic column is a gas-solid adsorption chromatographic column. In another embodiment, the chromatographic column is a gas-liquid gas chromatography column. In another embodiment, the trap further comprises an adsorbent material. In another embodiment, the filter is an activated charcoal filter. In another embodiment, the detector is selected from the group consisting of a photo ionization detector, a mass spectrometer, a spectrophotometer, and a thermal conductivity detector. In another embodiment, the detector is a photo ionization detector. In another embodiment, the pump provides negative pressure. In another embodiment, the system further comprises a housing. In another embodiment, the housing is no larger than 216 cubic inch.

In another aspect, the invention relates to a method of analyzing at least one chemical compound in a gas mix, the method comprising: directing flow of the gas mix through a trap to concentrate at least a quantity of the at least one chemical compound; redirecting flow of the gas mix through a filter to provide a filtered gas flow to the trap; releasing at least a quantity of the at least one concentrated chemical compound into the filtered gas flow; and analyzing at least a quantity of the released at least one concentrated chemical compound. In one embodiment, the at least one chemical compound comprises at least one organic compound. In another embodiment, the at least one organic compound comprises at least one volatile organic compound. In one embodiment, analysis of at least a quantity of the released at least one concentrated chemical compound comprises running at least a quantity of the released at least one concentrated chemical compound through a gas chromatography column. In one embodiment, the gas chromatography column is a gas-solid adsorption chromatographic column. In another embodiment, the chromatographic column is a gas-liquid gas chromatography column. In another embodiment, analysis of at least a quantity of the released at least one concentrated chemical compound comprises identifying the at least one organic compound by a method selected from the group consisting of photo ionization, mass spectrometry, spectrophotometry, and thermal conductivity. In another embodiment, analysis of at least a quantity of the released at least one concentrated chemical compound further comprises quantifying the at least one chemical compound. In one embodiment, the gas mix is an environmental gas mix. In another embodiment, the gas mix comprises gases exhaled or otherwise emitted by a living subject. In another embodiment, the gas mix is air.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising

FIG. 2, comprising

FIGS. 5A through 5D, depicts views of a spool around which a gas chromatography column is wound and a cover for same.

FIG. 6, comprising FIGS. 6A through 6E, depicts views of an oven and related components for a gas chromatography column.

FIGS. 7A and 7B, depicts two views of a block that surrounds the exterior of the adsorbent trap for heating and cooling.

FIG. 8, comprising FIGS. 8A and 8B, depicts two views of a component of a housing that contains the photo ionization detector, the component comprising an inlet port.

FIG. 10, comprising FIGS. 10A and 10B, depicts two views of a component of a housing that contains the photo ionization detector, the component comprising three holes for the detector pins, i.e., for power and signal.

DETAILED DESCRIPTION

Figure 1A:
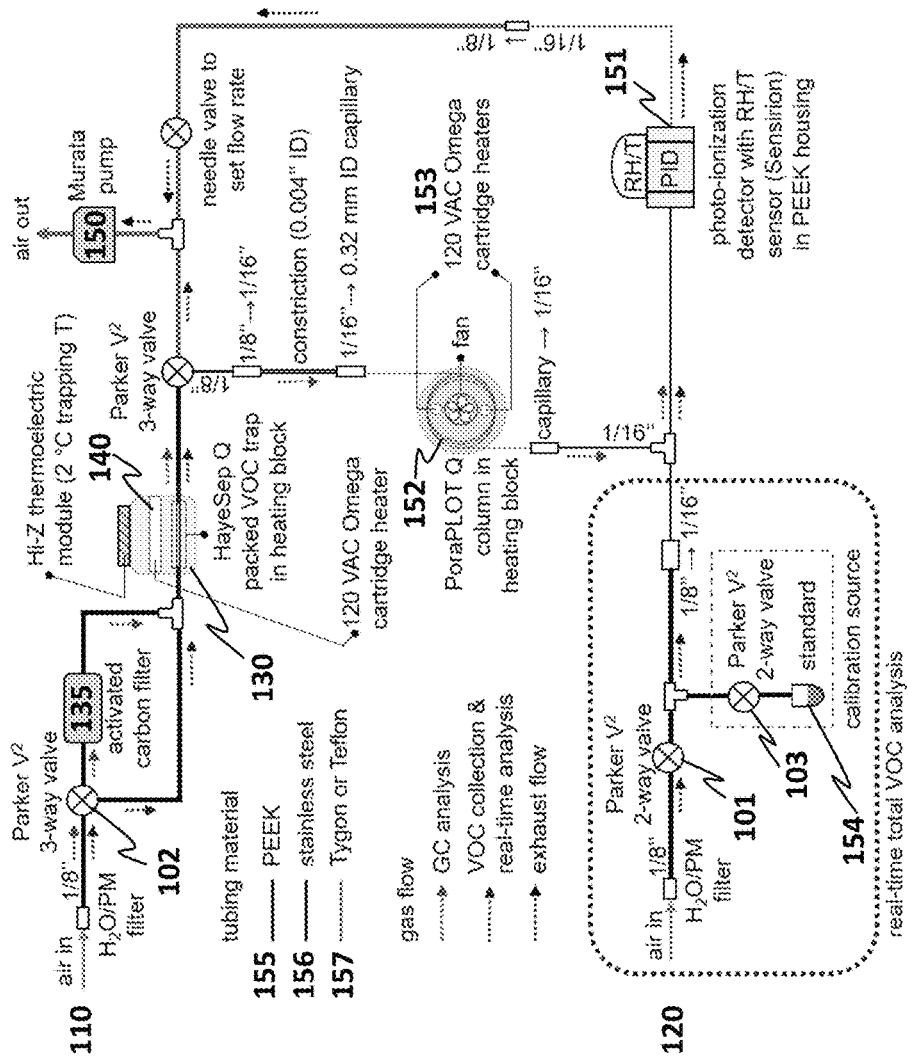
FIGS. 1A through 1H, is a schematic flow diagram of a system or an apparatus according to two embodiments of the invention, as they relate to the flow of gases, i.e., air, with or without analytes, through the system or apparatus.

The invention relates to a system for concentrating, identifying, and quantifying organic compounds in gas environments. The invention relates in particular to a micro monitor apparatus, a space-, time-, and cost-efficient device to concentrate, identify, and quantify organic compounds in gas environments. The invention further relates to a method centered on gas chromatography for identifying and quantifying organic compounds in gas environments, without the need for a compressed pre-bottled purified carrier gas.

The invention provides an unexpected advancement in analytical chemistry, as the method, the system and apparatus of the invention are designed to work without compressed gas, thus creating significant improvements over existing systems. Existing systems known in the art are big, cumbersome and expensive. On the other hand, an apparatus of the invention can be, in one embodiment, small, approx. 6"×6"×6", and low-cost, e.g., <$1000. In another embodiment, the system or apparatus of the invention is a monitor for organic compounds in the atmosphere or other gas environments, which are typically present at trace concentrations, e.g. parts per billion or parts per trillion. It provides simultaneous real-time measurements of total concentrations, and chemical resolution via periodic, gas chromatography without the use of compressed gas cylinders. The monitor provides unprecedented small, portable, and low-cost capabilities to identify and measure the prominent organic compounds.

The system or apparatus of the invention may be used for research or environmental monitoring at outdoor monitoring sites; indoors in industrial settings or in residences; as a low-cost health screening device through analysis of breath, other bodily substances or surfaces; or for other applications where organic compound measurements are critical (e.g. quality control for food, beverage, or chemical production; military monitoring, low-cost laboratory data collection; and monitoring volatile organics in water). A specific application is for use as a detector of Volatile Organic Compounds (VOCs) in air, compounds that are toxic and/or carcinogenic (e.g. benzene), and reactive precursors to ozone and secondary organic aerosol, which are the two types of air pollutants with the largest health effects.

The invention provides a functional, space-, time-, and cost-efficient apparatus and methods to concentrate, identify, and quantify organic compounds in gas environments, by, among other means, effectively replicating the capabilities of a gas chromatograph with the added feature of real-time measurements for high frequency data. The invention relies in part on a number of key advancements: (1) the ability to do gas chromatography of prominent organic compounds in gas streams using air, i.e., nitrogen ($N_2$), oxygen ($O_2$), and argon, with trace carbon dioxide ($CO_2$), water, and methane, drawn through a hydrophobic layer and a filter, as the carrier gas, and a small pump, rather than requiring high purity gas cylinders, i.e., large, costly high purity helium, hydrogen, and/or nitrogen from high pressure cylinders; (2) the small size and cost requires specially engineered parts and electronics, and thus creates the ability to use the device to take portable measurements or measurements at hard to access locations, including as part of networks made up of multiple devices; (3) simultaneous real-time measurements with 1 Hz frequency coupled with capabilities to identify the specific compounds with chromatography, something that could only be done before by a select few instruments larger in costs, size, and maintenance, e.g., Ionicon customized proton transfer reaction mass spectrometers. This results in research-grade high quality data on an extensive suite of organic compounds, especially those with 1 to 25 carbon atoms.

Definitions

It is to be understood that the figures and descriptions of the present invention have been simplified to illustrate elements that are relevant for a clear understanding of the present invention, while eliminating, for the purpose of clarity, other elements found in the art related to gas chromatography, gas stream purification, adsorption/desorption and/or trapping of organic compounds, detection of organic compounds, gas pumping, calibration of chromatographic systems, and the like. Those of ordinary skill in the art may recognize that other elements and/or steps are desirable and/or required in implementing the present invention. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods, materials and components similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

Detailed Description

Referring now in detail to the drawings, in which like reference numerals indicate like parts or elements throughout the several views, in various embodiments, presented herein are the system or apparatus, and methods for identifying and quantifying organic compounds in gas environments.

In one aspect, the invention relates to a system or apparatus comprising various components and devices capable of managing and analyzing gas flows. For example, as shown in FIG. 1A, an exemplary system 100 may include sampling inlets 110 and 120, adsorbent bed trap 130, filter 135, heater 140, pump 150, detector 151, chromatographic column 152, chromatographic column heater 153, calibration source 154, and conduits 155, 156 and 157 fluidly connecting these components as necessary. Sampling inlets 110 and 120 can be any type of standard port, with or without the capability of being shut off. The inlets can include hydrophobic membranes that reduce water entry. The adsorbent bed trap 130 can be made of any suitable material capable of reversibly adsorbing a chemical compound, in particular an organic compound, and more specifically a volatile organic compound. In some embodiments, the adsorbent trap may comprise silica gels and/or beads in a multi-layer configuration. Filter 135 can be made of any suitable type of filtration material capable of retaining a chemical compound, in particular an organic compound, and more specifically a volatile organic compound. In one embodiment, filter 135 is made of activated charcoal. Heater 140 can be any suitable heater, for example a cartridge heater, capable of heating adsorbent bed 130 and facilitate desorbtion of a chemical compound from adsorbent bed 130. Pump 150 can be any suitable pump capable of generating pressure for operating system 100. In one embodiment, pump 150 generates negative pressure. In another embodiment or flow scheme, the positive pressure exhaust of pump 150 can be used for desorption and/or gas chromatography via a valve upstream of some or all system elements. Detector 151 can be any suitable detector for sensing a chemical compound, in particular an organic compound, and more specifically a volatile organic compound. Chromatographic column 152 can be any suitable adsorbing surface, for example a gas chromatographic column. In some embodiments, the Chromatographic column comprises 100% Dimethylpolysiloxane (e.g. DB-1) or trifluoropropylmethyl polysiloxane (e.g. DB-200, DB-210) for the active phase. In other embodiments, the Chromatographic column is a porous polymer column, for example a Poraplot-Q column. The adsorptive materials used in the trap and Chromatographic column allow for efficient collection of analytes over long periods followed by thermal desorption and chromatographic separation of the materials in air. The system is advantageous because it protects the analytes and adsorbent materials from thermal degradation with oxygen. In this way, the system provides the ability to quantify individual analytes with higher precision than comparable equipment.

In some embodiments, the device may use traditional silica columns. In other embodiments, the device comprises passivated steel columns, for example RTX-1. Passivated steel columns provide faster and more accurate heating and cooling due to higher thermal conductivity, as well as more secure connections with traditional ferrules and fittings. As a result, the use of passivated steel columns increases reliability and reduces the amount of maintenance necessary in the field.

Chromatographic column heater 153 can be any suitable heater, for example a cartridge heater, capable of heating chromatographic column 152, in particular capable of generating a programmed temperature ramp. In some embodiments, the system of the present invention includes multiple heated zones. For example, the entire system including all transfer lines may be heated, in order to optimize transfer efficiency. In some embodiments, the column 152 and heater could be integrated into a "GC-on-a-chip", "column-on-a-chip" or "gas chromatograph-on-a-chip" arrangement, whereby the "column" is connecting grooves that are milled or etched into a plate made of any appropriate material known in the art, including but not limited to metal, silica, or glass. The etched or milled material may then be treated with an active column phase so that it behaves like a traditional column.

Calibration source 154 is any suitable calibration source for the appropriate detector and/or chromatographic column in use. In one embodiment, the calibration source comprises a single volatile organic compound. Conduits 155, 156 and 157 may be tubing made from materials such as, but not limited to, polyether ether ketone (PEEK), stainless steel, polytetrafluoroethylene (PTFE), or any other suitable material as would be understood by those skilled in the art.

In some embodiments, chromatography column 152 may utilize gas-liquid adsorption chromatography. In some embodiments, chromatography column 152 may comprise different active column "phases", i.e. adsorptive chemicals that are less prone to thermal degradation at high temperatures.

In one aspect, chromatography column 152 may utilize gas-solid adsorption chromatography which is less prone to degradation at high temperatures in the presence of oxygen in air. Another advantage of using a gas-solid adsorption chromatographic column is that it is less affected by water vapor or carbon dioxide. The gas-solid separation occurs across the trapping/concentrating adsorbent bed and the open tubular column that can be adapted with a variety of specific columns with different adsorbents, e.g., divinylbenzene, or molecular sieve. In one embodiment, the chromatography column is a column capable of using the major components of air as carrier gas, i.e., nitrogen and oxygen. Since nitrogen is the dominant component of air and similar in structure to oxygen, their performance as a carrier gas are similar.

In one embodiment, the system or apparatus are operated using vacuum gas chromatography, e.g., by providing a source of negative pressure. In another embodiment, the system or apparatus is operated using positive pressure gas chromatography. The differences between various embodiments depend on the orientation of the pump, valves, and connections, wherein a variety of configurations can be envisioned by one skilled in the art. In one embodiment, the system or apparatus employs elements of fast chromatography, e.g., a microbore column. In one embodiment, the microbore has a 0.05 to 0.15 mm inner diameter. In another embodiment, the column has a 0.15 to 1.00 mm inner diameter. In one embodiment, the microbore has a 0.53 mm inner diameter. In one embodiment, the chromatography column has a 0.05 to 1.00 mm inner diameter. In another embodiment, the chromatography column has a 0.53 mm inner diameter. In another embodiment, the system or apparatus employs other columns depending on target analytes and pump specifications. In other embodiments the system or apparatus uses a gas-liquid chromatography column that has a stationary phase resistant to oxygen degradation at the operating temperatures.

The system of the present invention may also include a coupled collection trap and chromatography control and analysis module, capable of adjusting flows (rate and direction) and temperatures in a way that is customizable to any particular set of analytes, but optimized for a broad range of analytes. In one example, the control and analysis module collects analytes in a cooled state at temperatures ≤5° C. for up to 15-30 minutes. In another example, the control and analysis module reverses the flow of air through the trap and supplies the trap with clean air through a charcoal filter. In another example, the module heats the trap rapidly to desorb analytes onto the column, cooled to <5-10° C. depending on the analytes. This or other examples may further comprise a cryotrap or cryofocusing element at the start of the column. Use of a cooling element in the trap and column presents an advantage over systems known in the art, because cooling the trap and the column allows for improved analyte retention, focusing, and performance. In yet another example, the module may begin operation with a set temperature hold, followed by heating the system at a pre-determined ramp rate, while adjusting the various flows to attain maximum separation efficiency of the column. In this or other examples, the system may further comprise a pressure constriction at the head of the column to optimize flow with a pump.

In another example, the system may begin collecting a second sample while still analyzing a first sample. The control and analysis module may accomplish this by opening a valve to a bypass line around the trap in gas-chromatography-only mode. This allows the rest of the gas chromatography analysis run to operate at a flow rate optimized for the latter portion of the run. In another example, the module executes a heating program and GC analysis, followed by a rapid cooling stage to prepare the system for the next analysis run.

As shown in FIG. 1A, system 100 comprises a detector 151. In one embodiment, detector 151 is a sensing element, such as a photoionization detector (PID), a miniature mass spectrometer, a spectrophotometer, a thermal conductivity detector, any other suitable spectrometer, or any other suitable detector. In one aspect, the invention relates to a system or apparatus employing photo ionization detection. Changing the ionization potential of the PID lamp, e.g., between 9.6-11.7 eV via changing the halogen gas inside the lamp, affords the apparatus bigger selectivity across a range of analytes with different ionization energies, i.e., from about 7 eV to about 11.7 eV. In one embodiment, the use of a 9.6 eV lamp allows selective ionization of aromatic hydrocarbons, also known as BTEX, and other compounds with ionization energies below 9.6 eV. Benzene, toluene, ethylbenzene, m&p-xylene, o-xylene, and 3-trimethylbenzene isomers are examples of compounds with ionization energies lower than 9.6 eV. In other examples, the ionization potential of the PID lamp is 10.0 eV, or 10.6 eV. In another embodiment, the use of a miniature mass spectrometer as a detector extends the tunable selectivity of the device.

Figure 2A:
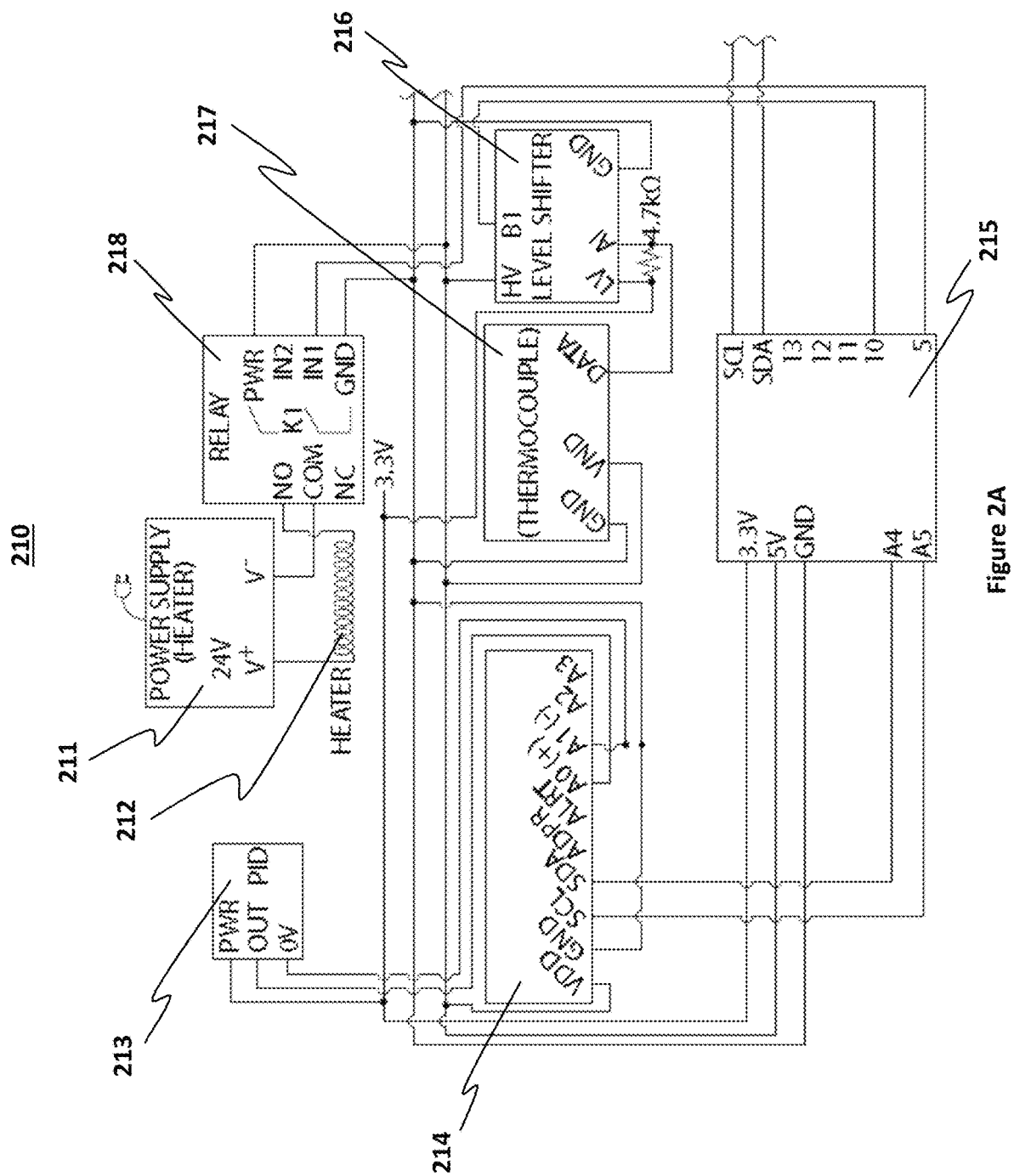
FIGS. 2A and 2B, is a partial schematic electric circuit of an apparatus according to one embodiment of the invention.
Figure 2B:
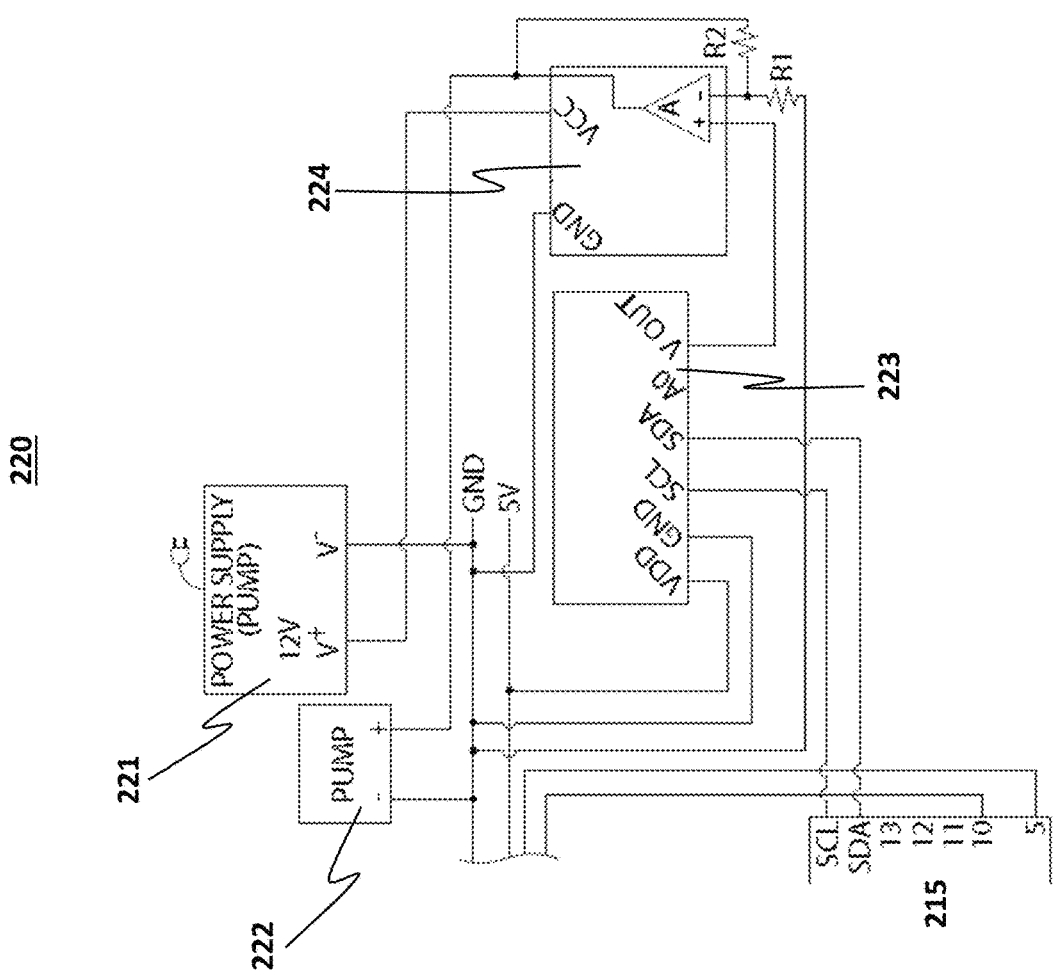

In one aspect, the invention relates to a system or an apparatus which is automated by a microprocessor and software that operates the system of valves, heaters, coolers, and collects data on the PID signal, relative humidity, pressure, and temperature across the system. In some embodiments, the collected relative humidity, pressure, and temperature data is used to correct data from the PID. In one embodiment, the system components such as those in the system of FIG. 1A may be electrically connected according to the schematic electric circuits 210 and 220 depicted in FIGS. 2A and 2B, respectively. In one embodiment, the components are selected from the group consisting of cartridge power supplies 211 and 221, heater 212, PID 213, analog to digital converter and gain amplifier 214, microcontroller 215, level shifter 216, thermocouple 217, relay 218, pump 222, digital to analog converter 223, and operational amplifier 224. In some embodiments, the control circuitry comprises at least one microcontroller, wherein some or all microcontrollers comprise multiple processing cores. In some embodiments, the microcontroller 215 comprises a single board computer (SBC), such as an Arduino®. In other embodiments, the microcontroller comprises a Programmable System on a Chip (PSoC), such as one manufactured by Cypress®. In other embodiments, the microcontroller comprises a Field-Programmable Gate Array (FPGA). In some embodiments, the control circuitry comprises ultra-low-noise circuits. In some embodiments, the control circuitry includes a wireless communication link, comprising wi-fi, cellular connectivity, BlueTooth® or any other wireless communication system known in the art. The wireless communication link allows for some or all of the functions of the system to be executed remotely, and some or all of the data collected to be transferred to a remote system for analysis. In some embodiments, the device may operate automatically without any user intervention, locally or remotely.

Figure 3:
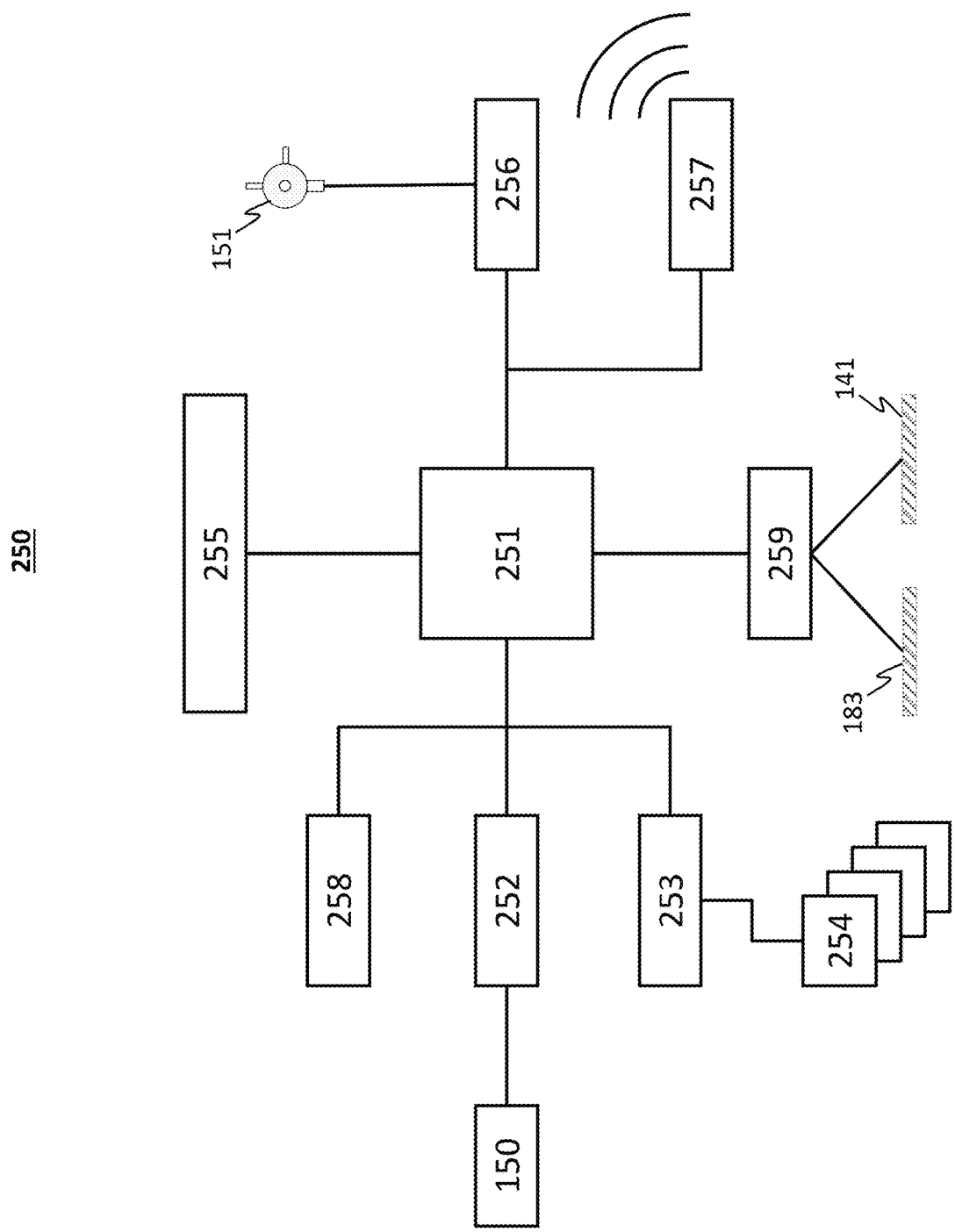
FIG. 3 is a simplified electrical diagram showing the control system according to one embodiment of the present invention.

Referring now to FIG. 3, a simplified control system diagram 250 of one embodiment of the present invention is shown. Microprocessor 251 executes a series of instructions which coordinates the collection of data from the various sensors and actuation of the various electrical and mechanical elements of the system. Microprocessor 251 is connected to pump controller 252, which in turn controls pump 150. Microprocessor 251 is further connected to a set of relays 253, PID data collector 256, environmental sensors 258, and Peltier Plate controller 259. Relays 253 are electrically connected to electronic valve actuators 254, which in turn mechanically control the various valves in the system in order to create the flow paths described in FIGS. 1C-1G, including but not limited to valves 102, 172, and 177. PID data collector 256 receives signals from PID 151 and converts that data into a form recordable by microprocessor 251. PID data collector 256 may also contain control circuitry for microprocessor 251 to send instructions to PID 151. Environmental sensors 258, periodically or on demand, sends environmental data to microprocessor 251 in order to facilitate control of the system. The environmental sensors may be any sensors from the set of temperature sensors, humidity sensors, pressure sensors, or any other sensors known in the art. Peltier plate controller 259 is electrically connected to Peltier plates 141 and 183, and through it the microprocessor 251 can independently regulate or disable the cooling function of plates 141 and 183. Microprocessor 251 is shown as a single element, but it is understood that the functions of microprocessor 251 may be split across multiple microprocessors in order to achieve higher efficiency. In one embodiment, control system diagram 250 includes a second microprocessor that controls the temperature-control elements of the system of the present invention, including the ovens and the Peltier plates.

In some embodiments, Microprocessor 251 is electrically connected to some combination of display 255 and wireless communication module 257. Display 255 displays system status and error messages in order to facilitate operation and troubleshooting of the system. In some embodiments, display 255 is an LCD display. Wireless communication module 257 facilitates communication between microprocessor 251 and a remote device. In some embodiments, the remote device periodically receives measurement information or system status data from the microprocessor 251. In some embodiments, the wireless communication device also receives control signals or commands from a remote device, allowing a remote user to exercise control over the functionality of the system.

With reference again to the exemplary system 100 of FIG. 1A, a gas stream, e.g., air, is pulled in through two sampling inlets, i.e., tubes, 110 and 120. In one embodiment, the gas is pulled by negative pressure via a pump 150 located at the far downstream end of the instrument. The real time inlet 120 is connected to a tube which leads directly to detector 151, i.e., PID, following an on/off valve 101. This stream of gas through the tube connected to inlet 120 provides real-time measurements of total organic compounds in the gas stream, or the total concentration of organic compound sensitive to the detection method.

Figures 5A, 5B:
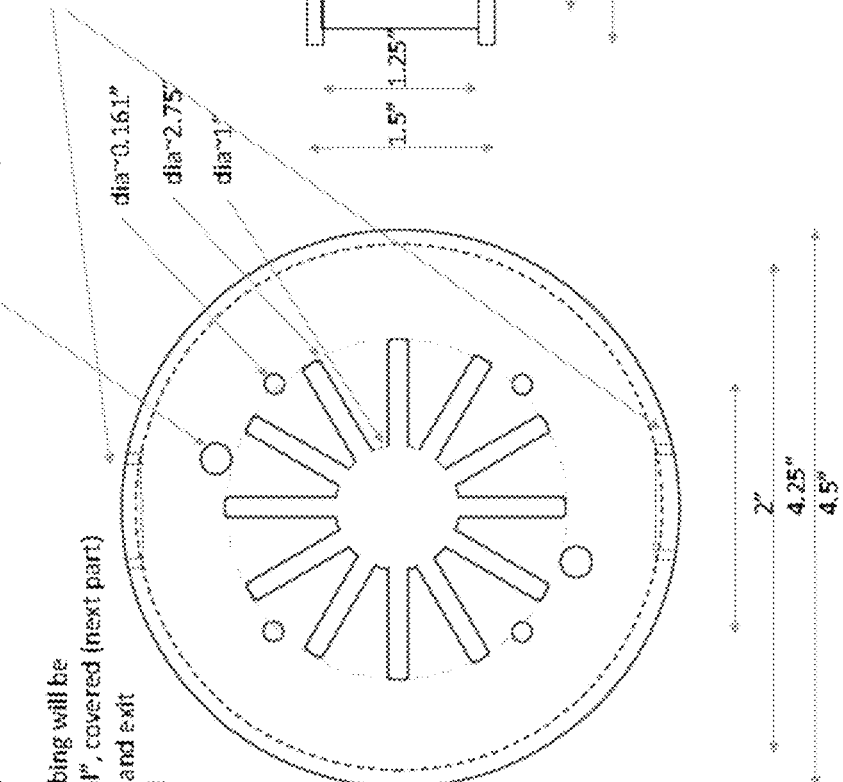
Figure 5:
FIG. 5, comprising
Figure 5:
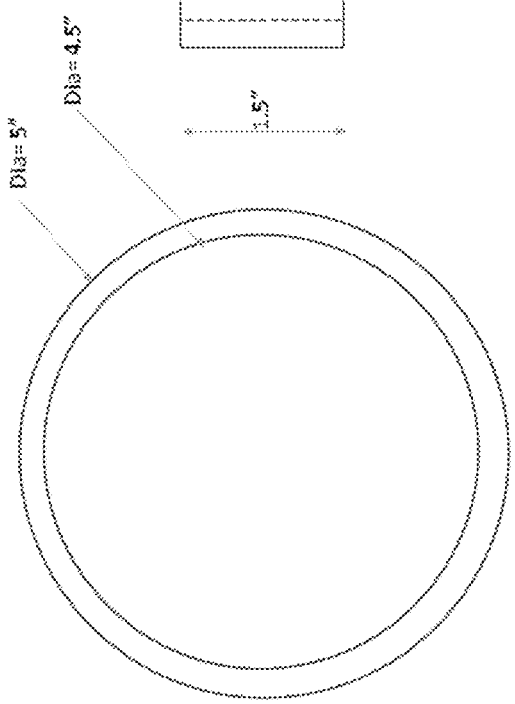

Inlet 110 concentrates the trace concentrations of organic gases onto an active, or inert, adsorbent surface or packed bed 130 that is thermoelectrically cooled in an aluminum block. In one embodiment, the adsorbent bed functions as a trap for the organic gases. After an adjustable time interval of concentrating trace organics, a valve 102 switches to draw air in through a charcoal filter 135 that provides air free of organic compounds. In one embodiment, the time interval is between 2 and 30 minutes. The on/off valve 101 on the "real-time" inlet is activated so that all flow is directed through the charcoal filter providing clean air which acts as the carrier gas for a chromatographic column 152. The flow of clean air from inlet 110 is directed through the charcoal filter 135, the adsorbent bed 130, and then into a gas chromatography column 152. The adsorbent bed/surface 130 is slowly heated, for example by heater 140, to thermally desorb, or release, the organic compounds as a function of their vapor pressure or polarity, effectively providing a rough separation method. The effluents from this trap proceed into a capillary gas chromatography column 152 that operates on the principle of gas-solid adsorption chromatography, or gas-liquid chromatography. In one embodiment, the gas chromatography column is replaced by a gas chromatography microfluidic chip. The column is wrapped around a custom-machined aluminum cylinder, or the microfluidic chip is placed against an aluminum block, that is heated by heating cartridges 153 at a rate that further separates/resolves the analytes in the column. In one embodiment, the column is positioned within a custom-machined aluminum oven. In one embodiment, the aluminum cylinder is as described in FIGS. 5A and 5B machined in the shape of a spool. In another embodiment, the cylinder comprises various machined indentations, cavities or channels which can be used for, but not limited to, fixation of the cylinder to the rest of the apparatus, for appending heating/cooling elements, or for venting. In another embodiment, the cylinder further comprises two grooves in the edge of the spool for entrance/exit of the chromatographic column. In another embodiment, the cylinder is covered by a cylindrical cover as described in FIGS. 5C and 5D.

Figure 6C:
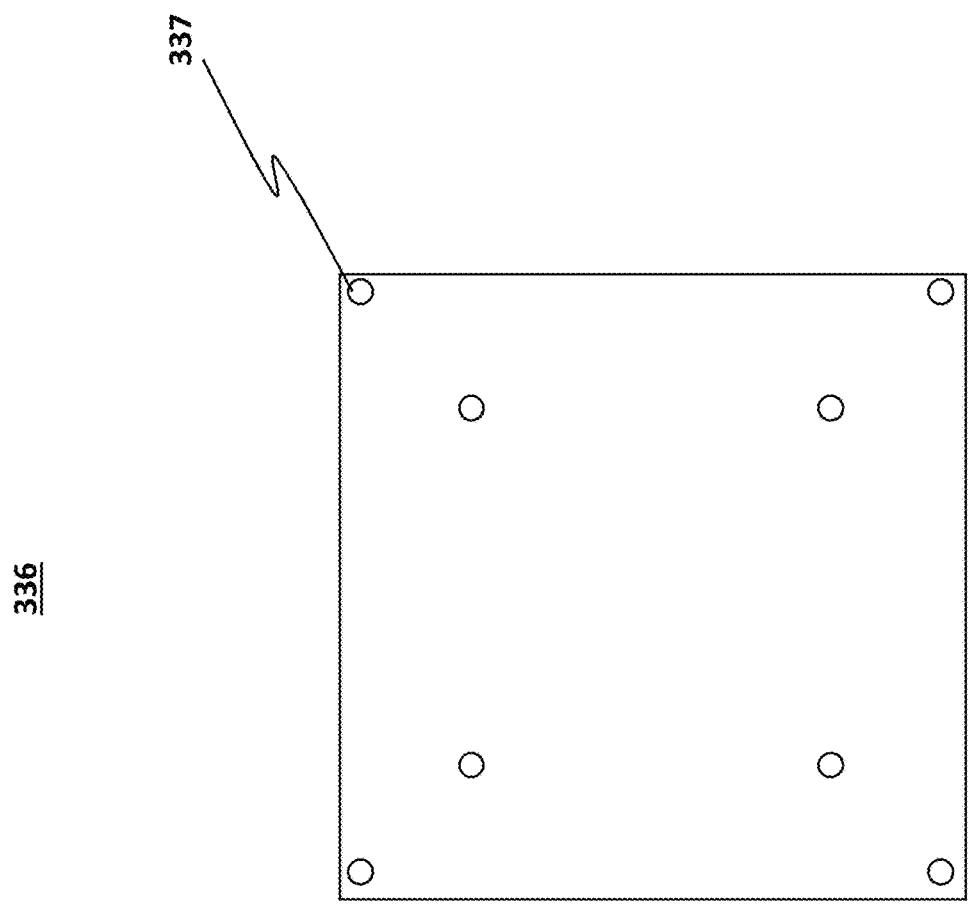
Figure 6D:
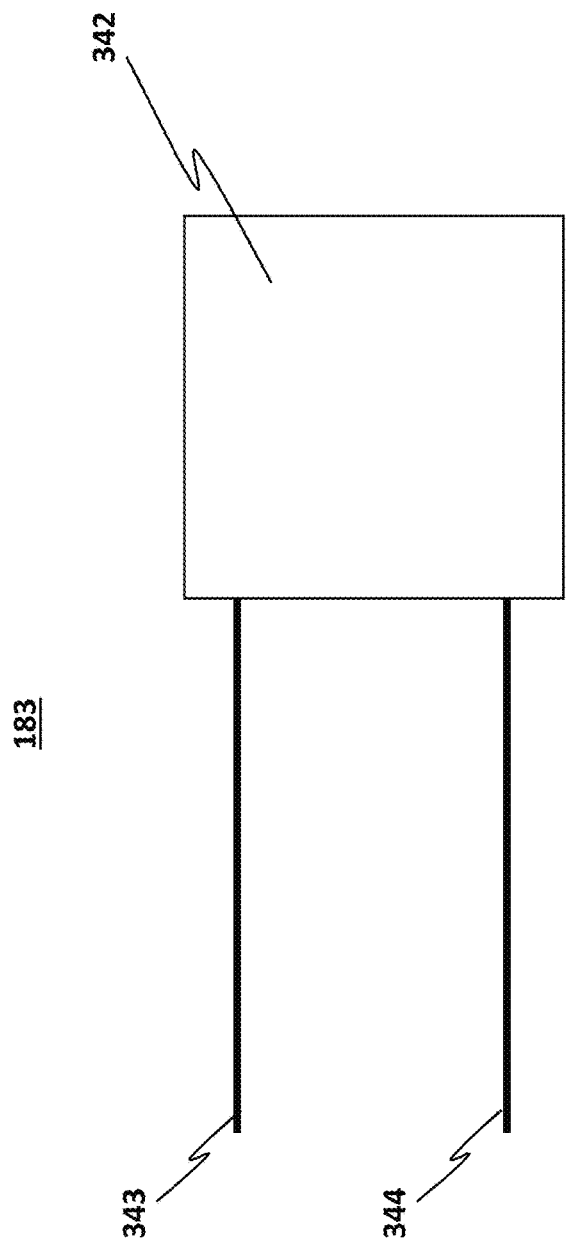
Figure 6E:
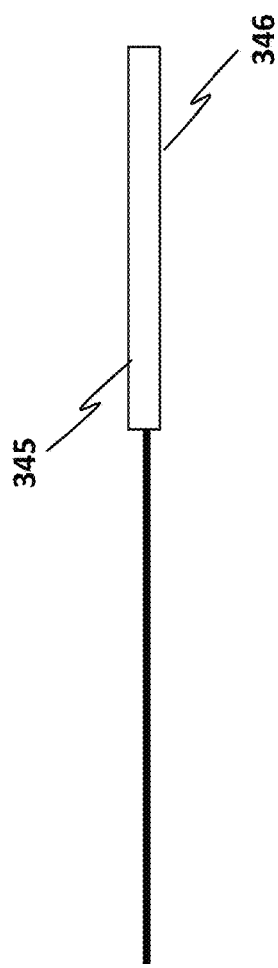

Another embodiment of the oven is shown in 331 in FIGS. 6A-6E. In this embodiment, the oven is an aluminum housing as shown in FIG. 6A, depicting a top view, and FIG. 6B, depicting a front view. The oven may comprise machined aluminum, and comprises mounting holes 333 and a set of evenly spaced holes 332 in a circular pattern. The chromatographic tubing enters the oven 331 through inlet/outlet holes 334 or 335, then wraps around the holes 332 before exiting the oven through the other of inlet/outlet holes 334 or 335. The oven is enclosed with oven cover 336 shown in FIG. 6C, comprising mounting holes 337 that correspond to mounting holes 333. In some embodiments, the oven further comprises Peltier plate 183 shown in FIG. 6D, showing a front view, and FIG. 6E, showing a side view. Peltier plate 183 comprises plate 342 which generates a temperature differential between cold side 345 and hot side 346 in response to electric current provided through wires 343 and 344. Plate 342 operates based on the thermoelectric effect, also known in the art as the Peltier effect. In some embodiments, a heat sink comprising one or more fins may be affixed to the hot side 346 of Peltier plate 183 to increase the effectiveness of heat transfer from cold side 345 to hot side 346.

The effluent from the chromatographic column 152 enters the PID 151, or other detector, where the mass of each compound is quantified based on the PID signal, and an atmospheric concentration can be calculated via the known concentrating flow rate during sampling. Similar to normal chromatography, the identity of each compound can be reliably determined based on the time it elutes from the column-adsorbent bed system that is heated with the same heating program each run. Following completion, valve 101 opens and the system reverts to real-time measurements and the chromatography inlet cools via fans and thermoelectric coolers. Following the PID, both flows exit via pump 150. A built-in calibration method is controlled by an on/off valve 103. In one embodiment, the system effuses a constant amount of evaporating calibrant, e.g., a single VOC, through a critical orifice into one of the sample inlets, which is periodically used to calibrate the system. In one embodiment, the calibrant in vessel 154 is introduced through the real time inlet. Consistent, known, or calibrated relative response factors for the PID allow for cross-calibration to all the other measured compounds.

Figure 1B:
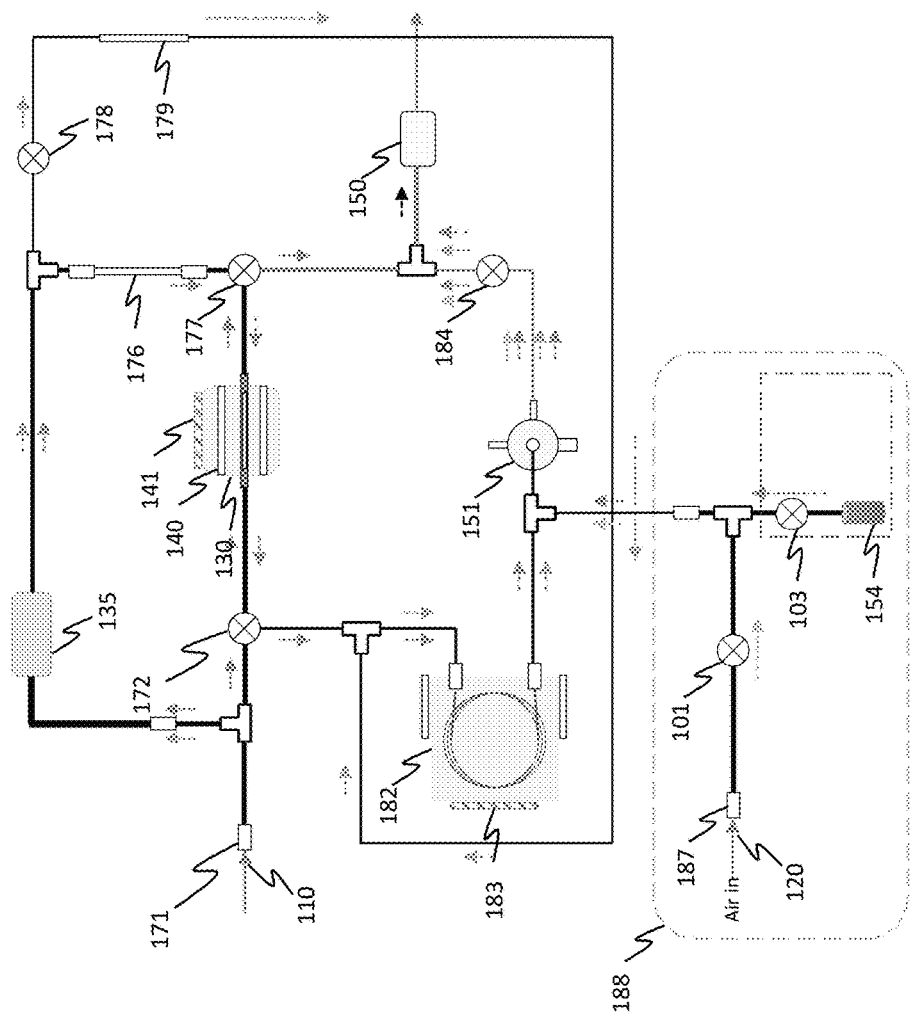
Figure 1C:
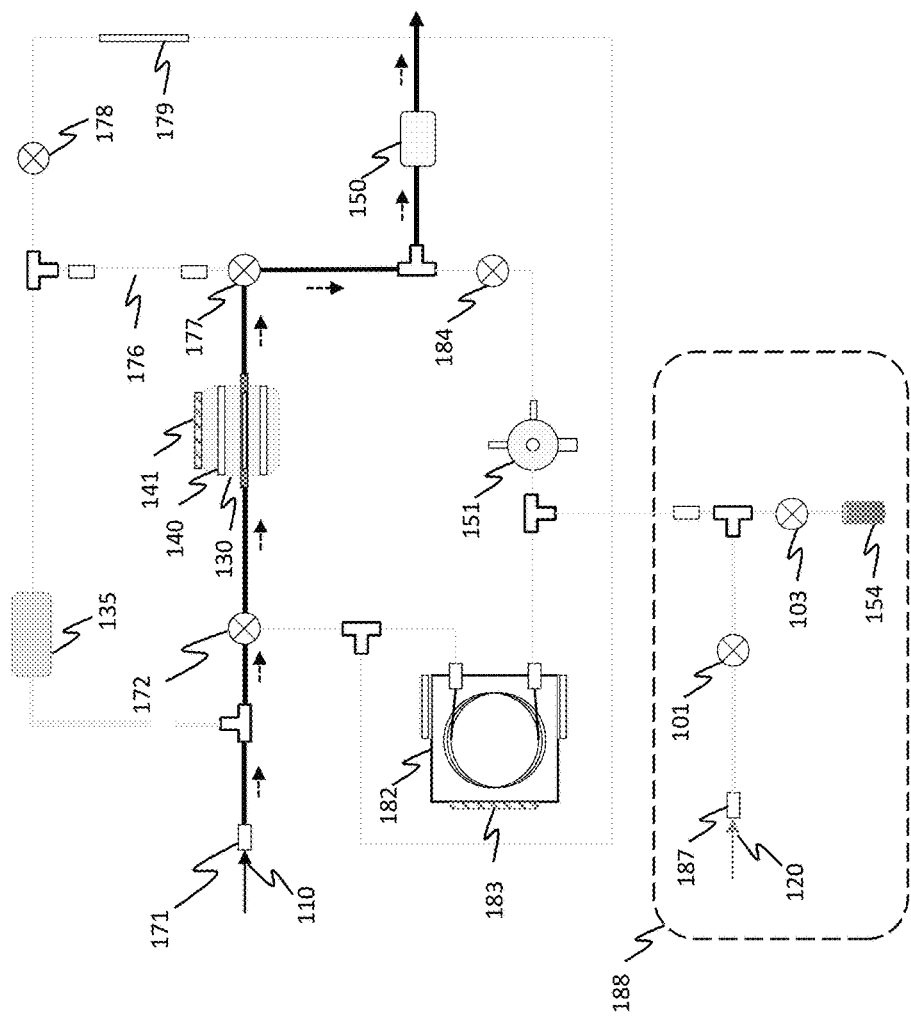
Figure 1D:
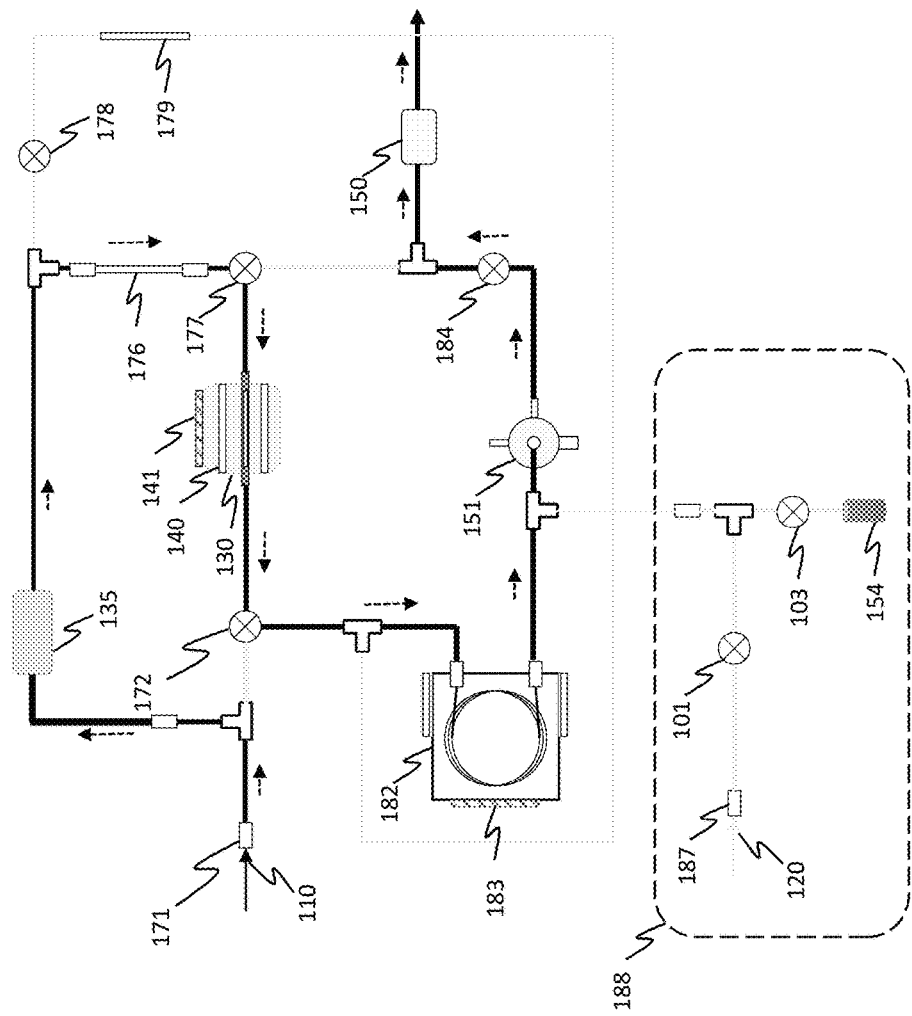
Figure 1E:
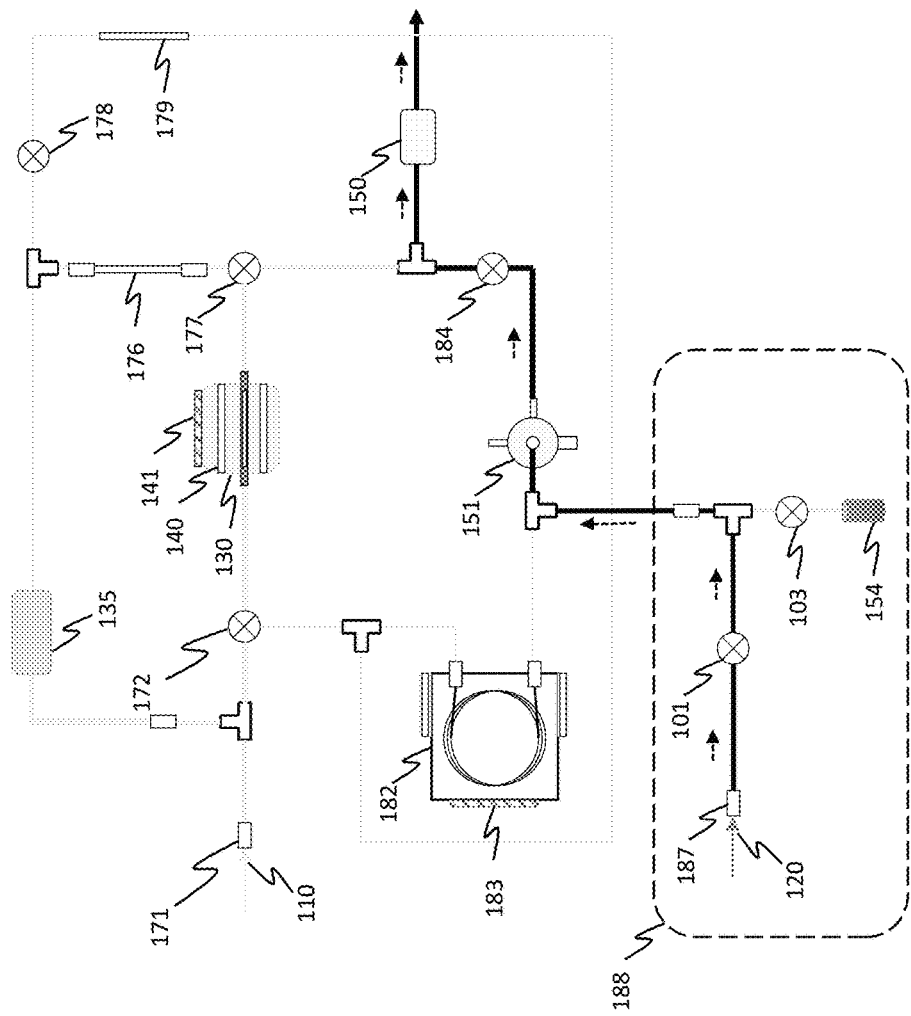
Figure 1F:
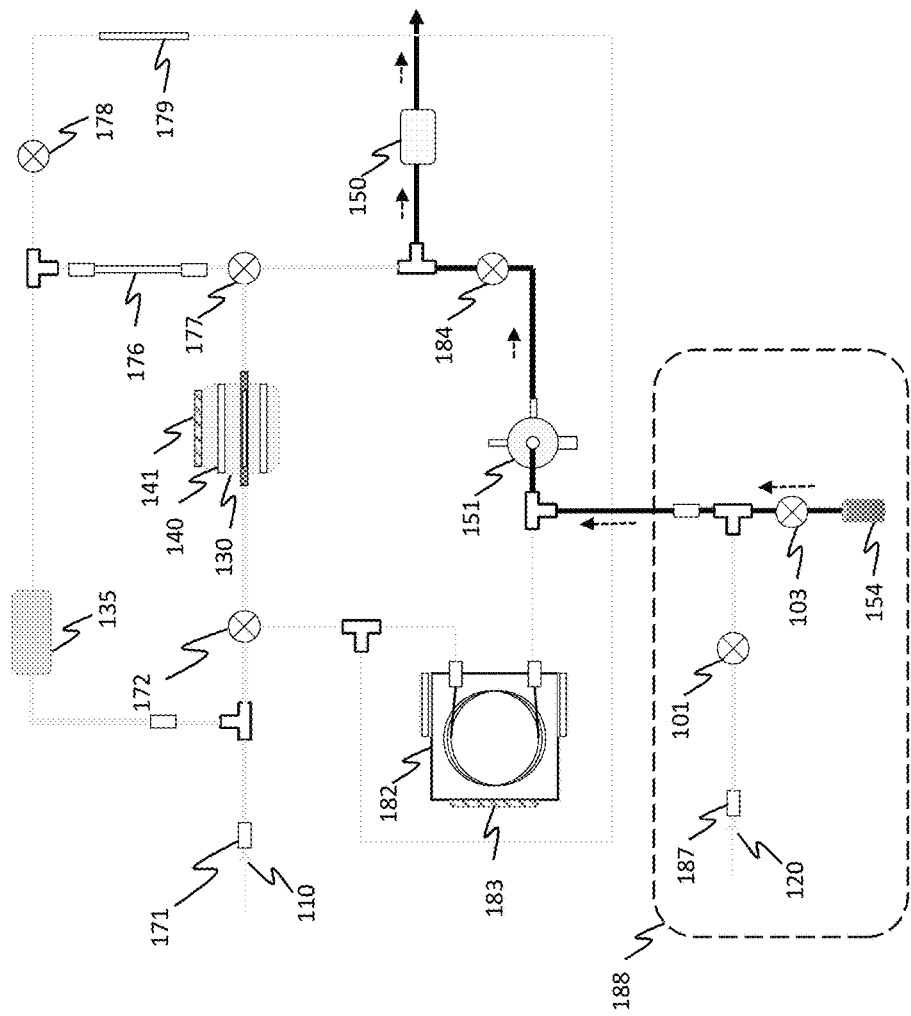
Figure 1G:
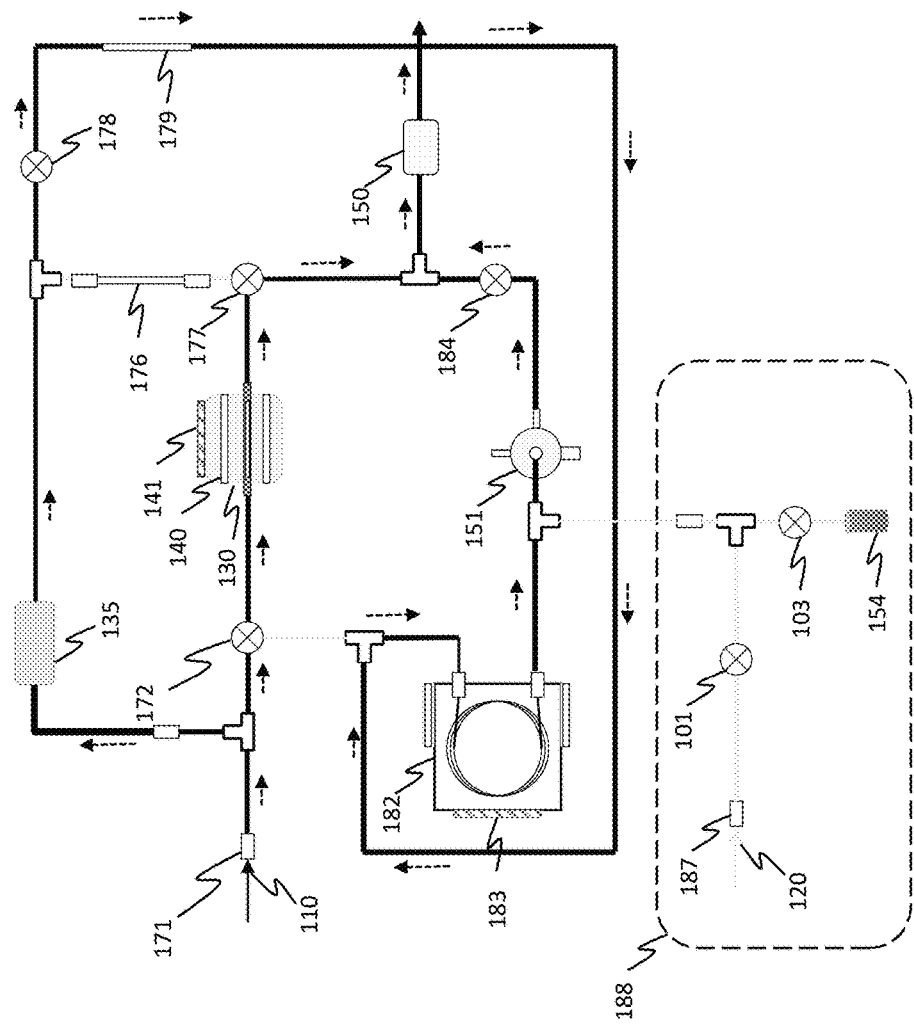
Figure 1H:
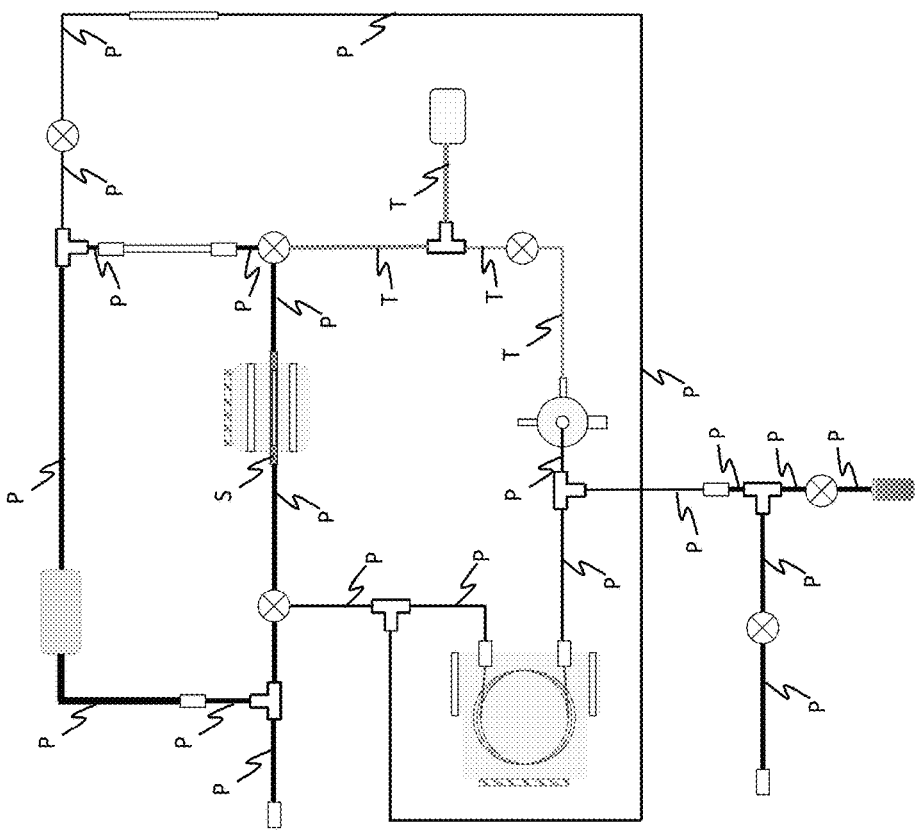

Another embodiment of the invention is described in system 160 of FIGS. 1B-1H. System 160 of FIG. 1B shows the overall structure of the various parts and how they are connected. FIGS. 1C-1G depict flow diagrams of the various modes of system 160. Particularly, FIG. 1C depicts the Trap mode, FIG. 1D depicts the Desorb/Run mode, FIG. 1E depicts the Real-Time mode, FIG. 1F depicts the Calibration mode, and FIG. 1G depicts the Trap-and-Run mode. The operation of system 160 is similar to the operation of system 100, but with the added step of reversing the flow of air through the adsorbent trap 130 in between the trapping step and the desorbing step. FIG. 1H shows the materials used in one embodiment of the invention.

Referring to FIG. 1C, the flow diagram 161 of the Trap mode of system 160 is shown. A vacuum is created by the pump 150 and unfiltered air enters through the inlet 110. Air proceeds first through a hydrophobic PM filter 171 before being routed by valve 172 through the near end of the adsorbent trap 130, where some compounds are trapped via adsorption for later analysis. In some embodiments, the trap may be cooled using peltier plate 141. Cooling the trap 130 allows for improved analyte retention, focusing, and performance. The remaining air proceeds through valve 177 and out of the system through the pump 150.

Referring now to FIG. 1D, a flow diagram 162 of the Desorb/Run mode of system 160 is shown. Once the trapping step is complete, the adsorbent trap 130 contains some compounds to be analyzed. Valves 172 and 177 change the flow direction as shown in flow diagram 162, driving unfiltered air through the inlet 110 followed by hydrophobic PM filter 171, then routing the unfiltered air through activated carbon filter 135 to remove most compounds and send filtered air through the system. The filtered air proceeds through flow constrictor 176 before entering the adsorbent trap 130 through the far end, a flow direction opposed to the flow of diagram 161. In some embodiments, a heater or heaters 140 are engaged during the Desorb/Run mode 162, speeding the rate at which compounds desorb from the adsorbent trap 130. The desorbed compounds, entrained in the filtered air, proceed through valve 172 to capillary gas chromatography column 182, which also may optionally be heated. Column 182 operates similarly to column 152 of FIG. 1A. The effluent from column 182 enters PID or other detector 151, where the mass of each compound is quantified. Finally, air proceeds through valve 184 and pump 150 before exiting the system. In some embodiments, the system further comprises Peltier plate 183, which is affixed to oven 182 and provides thermoelectric cooling in some phases of system air flow.

The flow constrictor 176 functions to restrict flow prior to entering the adsorptive trap and the column, ensuring that pressure is low across the whole column and increasing resolving potential (i.e. the number of "plates" in the column). This presents significant advantages over similar systems known in the art.

FIG. 1E depicts a flow diagram 163 of the Real-Time mode of system 160. In real-time mode, flow is similar to real-time mode of the system 100 of the present invention. Unfiltered air enters through a secondary inlet 120 and then through hydrophobic PM filter 187, before proceeding through valve 101 directly to PID or other detector 151. The air then flows through valve 184 and out of the system via pump 150. One advantage of the system of the present invention is the ability to continuously monitor in real-time mode, while periodically switching to a fuller GC analysis described in FIGS. 1C, 1D, and 1F. In some embodiments, a high reading or spike in total concentrations detected during real-time sampling triggers a switch to trap-and-run mode, thereby allowing for more precise measurement of the chemical composition of the detected compounds. In some embodiments, the trap-and-run measurements may be used to discern the source of one or more chemical compounds.

A further operating mode is contemplated by combining the flow paths of FIGS. 1C and 1E. In embodiments of the device that support the real-time flow path 163, the system of the present invention may collect compounds continuously via flow path 163 while simultaneously collecting compounds in the trap via trap flow path 161. In such a "real-time and trap" mode, the system may collect high time-resolution data of total concentrations (real-time data) then at the end of the collection period, the compounds from the trap may be analyzed to determine the chemical speciation of the mixture over the period during which high time resolution data was collected. This mode is of particular use to capture events that happen over short periods where the duration and features of the event are of interest and where it is also advantageous to know the chemical speciation of the mixture over that period.

FIG. 1F depicts a flow diagram 164 of Calibration mode of system 160. Operation of calibration mode is similar to that of real-time mode 163, except that instead of running unfiltered air through the system from the inlet of filter 187, valve 101 closes and valve 103 opens to pull in a constant amount of a standard evaporating calibrant 154. Similarly to the calibration flow of system 100, calibration mode 164 compares the results of from detector 151 with known relative response factors, allowing for cross-calibration to other measured compounds.

FIG. 1G depicts a flow diagram 165 of the Trap-and-Run mode of system 160. In this mode, two parallel flow pathways are opened at once. In the first path, unfiltered air enters inlet 110 and proceeds through filter 171 to charcoal filter 135. The filtered air runs through valve 178 and flow constrictor 179 before passing through the column 182, in which organic particles from a previous run are already present. In some embodiments, the flow constrictor 179 may be of a different size, such that the flow rate of the filtered air through the column may be adjusted or optimized to be more effective for separating and detecting compounds. The organic particles are freed and pass, entrained in filtered air, into PID or other detector 151 before being pumped out of the system by pump 150. Simultaneous to the first flow, a second flow path pulls unfiltered air through filter 171 then through valve 172 into trap 130, where some particles become trapped for a future run.

By alternating between this mode and the desorb/run mode depicted in FIG. 1D, the system of the present invention can run more efficiently and spend more time sampling.

FIG. 1H depicts the various materials used in the flow conduits in certain embodiments of the invention. Segments labeled with a "P" comprise polyether ether ketone (PEEK). Segments labeled with an "S" comprise stainless steel. Segments labeled with a "T" comprise Tygon or Teflon. The materials described herein are not meant to be limiting, but merely depict an example of the materials that could be used in certain configurations of the system of the present invention.

Figure 4:
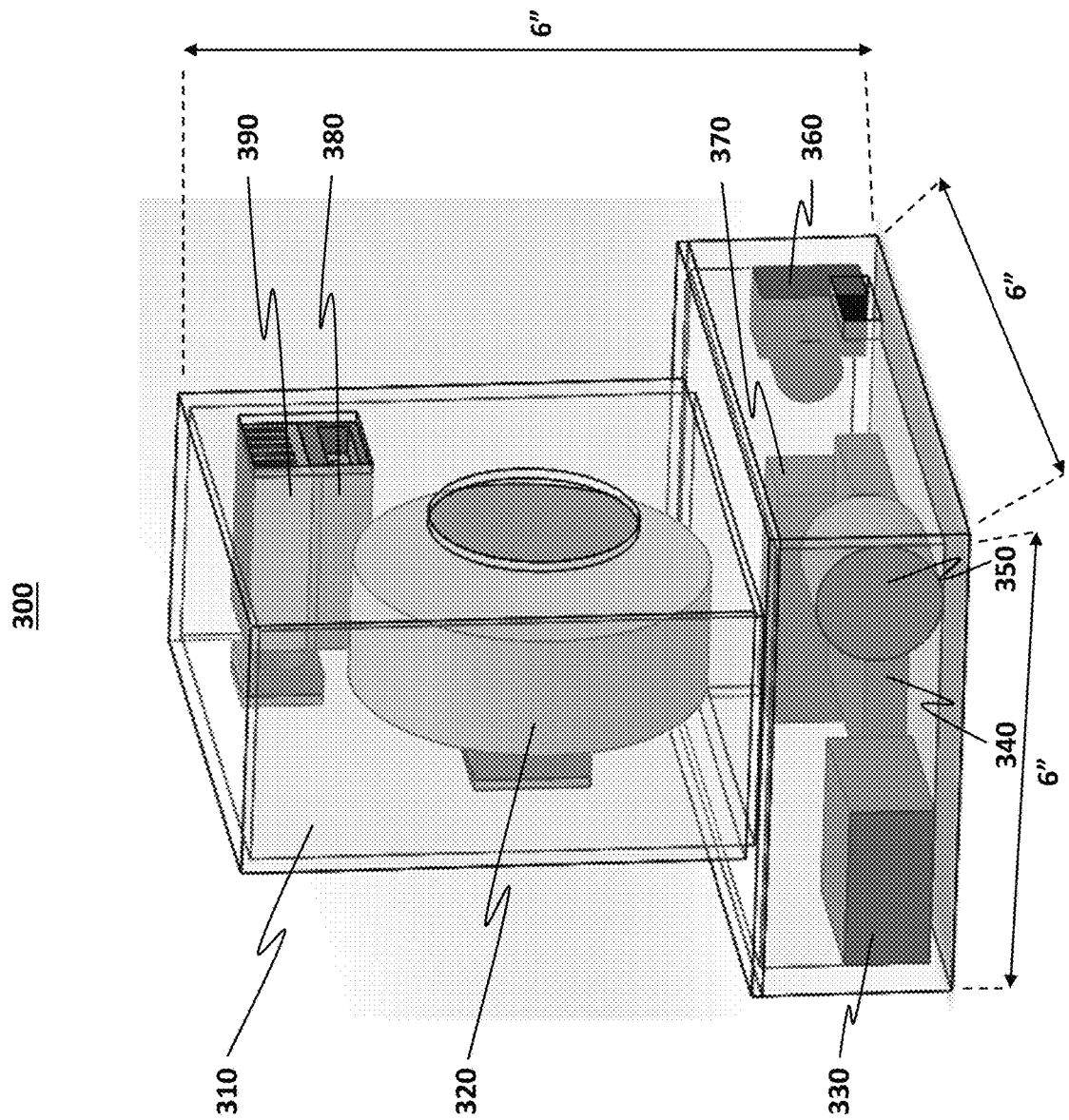
FIG. 4 is a perspective view of an apparatus according to one embodiment of the invention.
Figure 7:
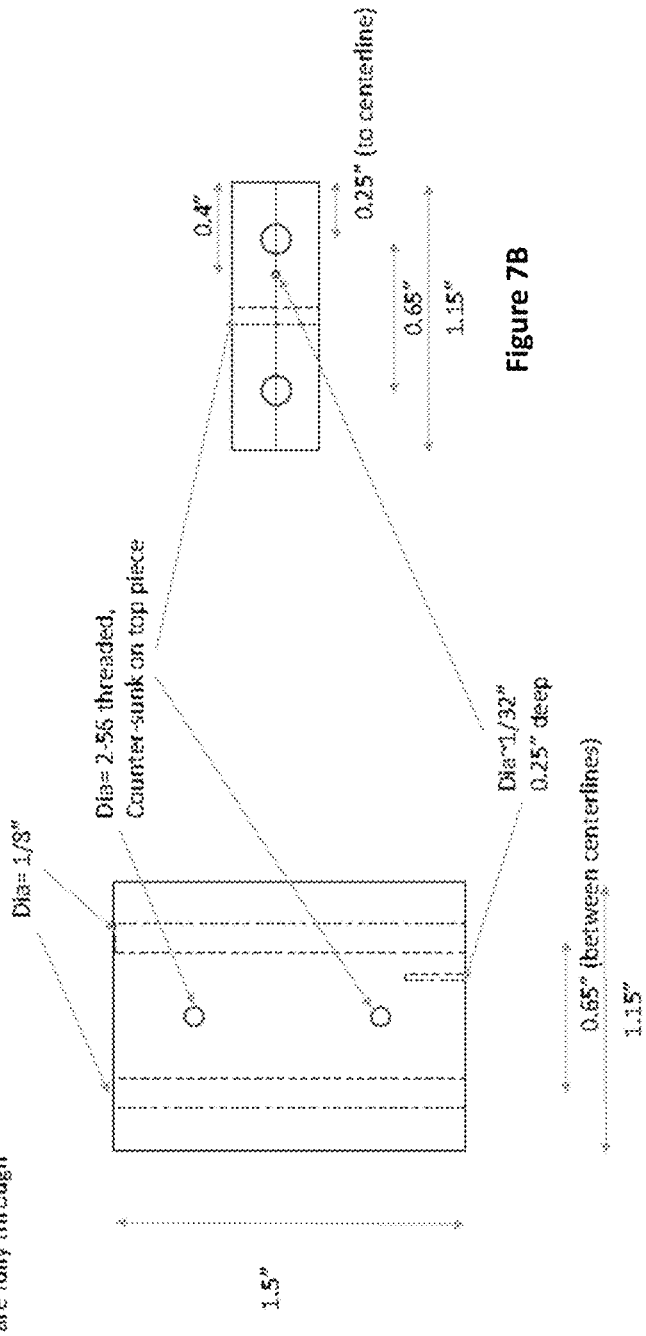
FIG. 7, comprising

In another aspect, the system components may be housed in a single or multi-compartment apparatus 300 as described in FIG. 4. In one embodiment, the size of the apparatus is about 6"×6"×6", or no more than 216 cubic inch in volume. In one embodiment, the apparatus includes various parts, e.g., a housing 310, a column oven and spool 320, a power supply 330, a microcontroller and custom circuit board(s) 340, a detector housing 350, a pump 360, a calibration unit and activated carbon filter 370, a trap heating and cooling block 380, and trap cooling fins 390. In one embodiment, the gas chromatography unit 320 further comprises cylindrical parts 321 and 322. As described elsewhere herein, cylinder 321 can be machined as a spool on which a chromatographic column can be wound. In one embodiment, the apparatus of the invention further comprises block 381 as shown in FIGS. 7A and 7B, that surrounds the exterior of the adsorbent trap for heating and cooling. In another embodiment, the apparatus of the invention comprises block 382 as shown in FIG. 7C (depicting a front view) and 7D (depicting a top view). The block heater or heaters may be positioned in channels 385. In some embodiments, block 382 comprises two halves separated at a center seam 386. In some embodiments, thermal couple is positioned in hole 384 to monitor the temperature of the block.

Figure 9C:
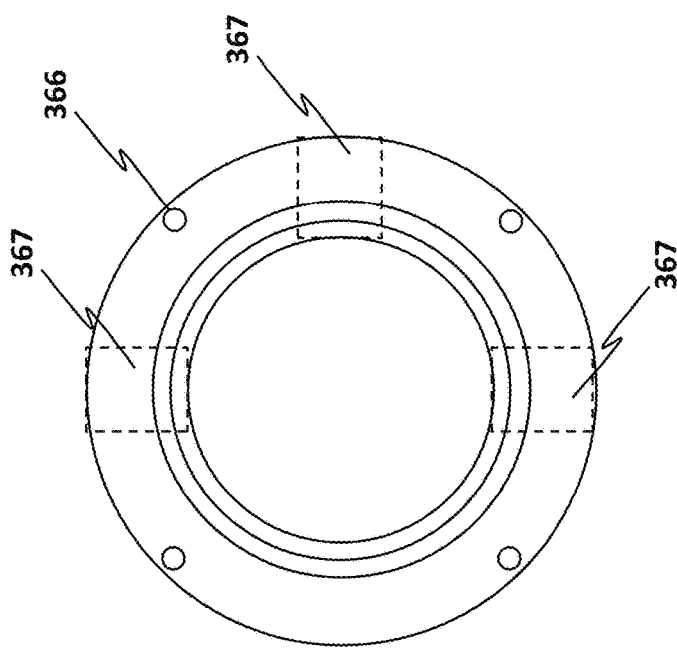
FIG. 9, comprising
FIGS. 9A and 9B, depicts two views of a component of a housing that contains the photo ionization detector, the component comprising an outlet port.

In one embodiment, the apparatus of the invention further comprises a component 351 of housing 350 that contains the photo ionization detector, component 351 comprising an inlet port. In another embodiment, the apparatus of the invention further comprises a component 352 of housing 350 that contains the photo ionization detector, component 352 comprising an outlet port. In an alternate embodiment shown in FIG. 9C, the apparatus of the invention further comprises a component 362 of housing 350 that contains the photo ionization detector, component 362 comprising multiple outlet ports 367 and mounting holes 366.

In another embodiment, the apparatus of the invention further comprises component 353 of housing 350 that contains the photo ionization detector, component 353 comprising three holes for the detector pins, i.e., for power and signal. In one embodiment, the parts are connected according to schematic 100. In another embodiment, the parts are connected according to schematics 210 and 220.

One additional advantage of the small size of the system of the present invention is that the column oven 331 has a lower mass than would typically be needed, and thus also a lower thermal mass. Ovens with lower thermal mass are capable of tighter temperature regulation because they are capable of storing (and re-radiating) less heat than larger ovens, allowing them to cool faster when power is removed.

Figure 13:
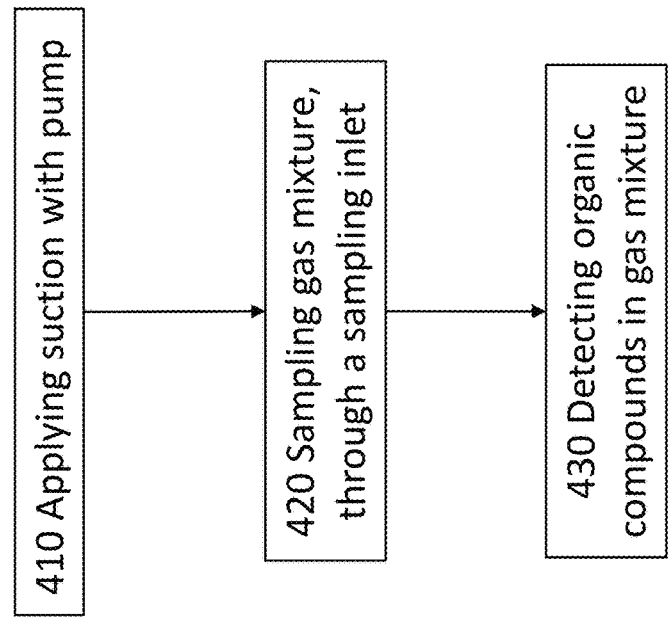
FIG. 13 is a flow chart of a real-time analysis method for identifying and quantifying organic compounds in gas environments according to one embodiment of the invention.

In other aspects, the invention relates to methods for identifying and quantifying organic compounds in gas environments. Referring to FIG. 13, an exemplary method of a real-time analysis 400 is shown. In one embodiment, the real-time analysis method 400 comprises step 410 of applying either positive or negative pressure, e.g., applying suction with a pump, which will force a gas mix through a system or apparatus, e.g., a system or apparatus of the invention. Real-time analysis method 400 further comprises step 420 of sampling a gas mixture, e.g., air, through a sampling inlet, e.g. sampling inlet 120 as shown in FIG. 1A as part of system 100. Real-time analysis method 400 further comprises step 430 of detecting organic compounds in a gas mixture. Detection can be accomplished by a PID detector such as for example detector 151 as shown in FIG. 1A as part of system 100.

Figure 14:
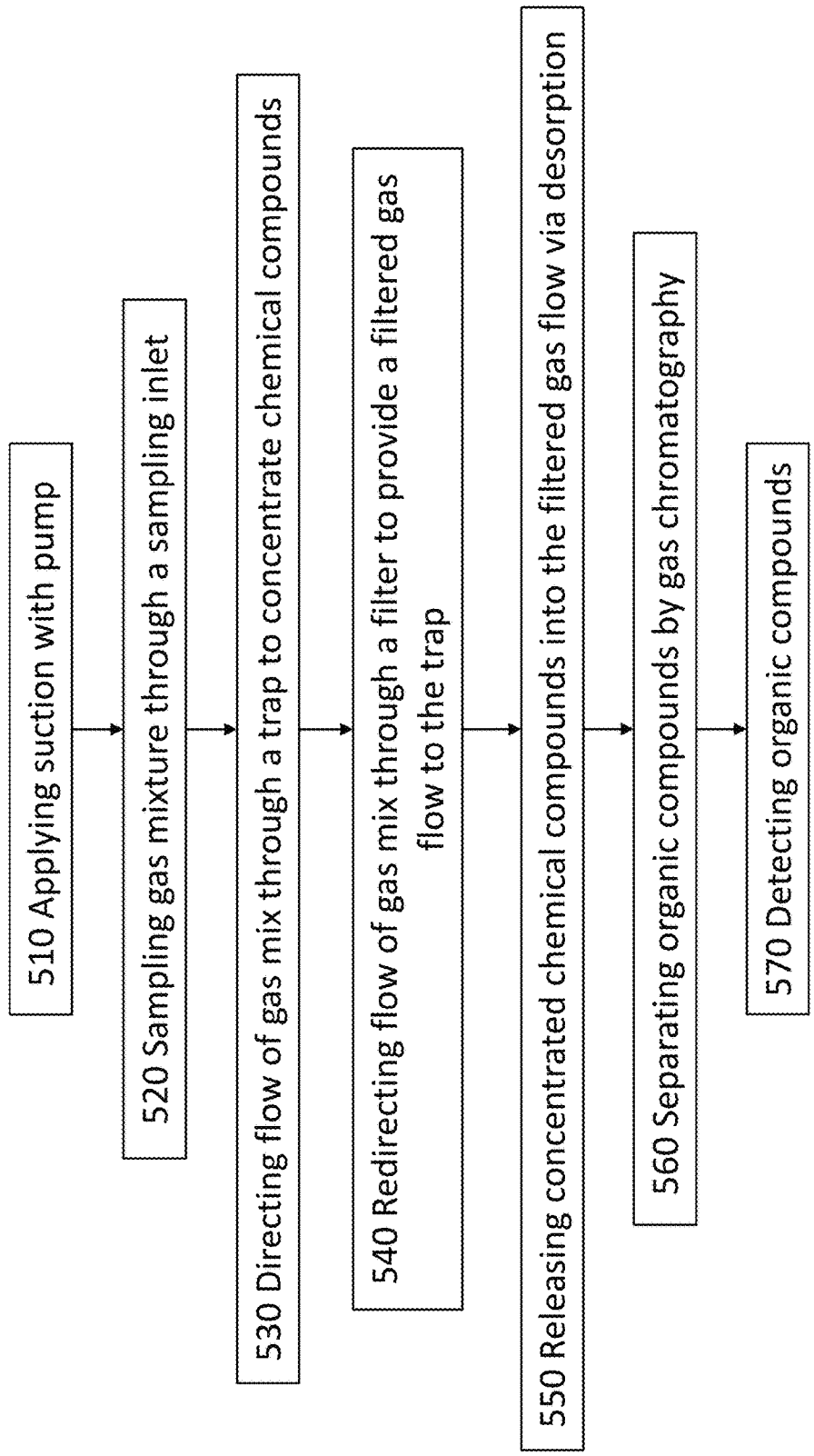
FIG. 14 is a flow chart of a gas chromatography method for identifying and quantifying organic compounds in gas environments according to one embodiment of the invention.

In another aspect, the invention relates to a method for identifying and quantifying organic compounds in gas environments, the method comprising a chromatography step. In one embodiment, the chromatography step is performed without the need for a compressed pre-bottled purified carrier gas, but rather by using purified air as a carrier gas. As shown in FIG. 14, in one embodiment the method is gas chromatography analysis method 500. Gas chromatography analysis method 500 comprises step 510 of applying either positive or negative pressure, e.g., applying suction with a pump, which will force a gas mix through a system or apparatus, e.g., a system or apparatus of the invention. Method 500 further comprises step 520 of sampling a gas mixture, e.g., environmental air, through a sampling inlet, e.g. sampling inlet 110 as shown in FIG. 1A as part of system 100. Gas chromatography analysis method 500 further comprises step 530 of directing flow of the gas mix through a trap to concentrate at least a quantity of a chemical compound, wherein the organic compound is trapped on a bed of adsorbent material 130 such as shown for example in FIG. 1A as part of system 100. Method 500 further comprises step 540 of redirecting flow of the gas mix through a filter to provide a filtered gas flow to the trap, thus providing gas mix, e.g., air, free of organic compounds. Step 540 of method 500 can be accomplished for example by diverting the flow of sampled gas through an activated carbon filter 135, for example as shown in FIG. 1A as part of system 100. Filtration removes all or part of the organic compounds in order to provide clean carrier gas, e.g., clean air. Gas chromatography analysis method 500 further comprises step 550 of releasing at least a quantity of concentrated chemical compounds into the filtered gas flow, for example by sequential thermal desorption of organic compounds, wherein the previously trapped organic compounds are desorbed from the bed of adsorbent material 130 by slowly increasing temperature, for example by using a heater 140 as shown in FIG. 1A as part of system 100. Gas chromatography analysis method 500 further comprises step 560 of separating at least a quantity of the released concentrated chemical compounds. In one embodiment, the separation comprises separating organic compounds, e.g., by gas chromatography. Organic compounds desorbed from the bed of adsorbent material are entrained by clean air provided by filtration into a chromatographic column, for example column 152 as shown in FIG. 1A as part of system 100. Gas chromatography analysis method 500 further comprises step 570 of detecting organic compounds in the chromatographic column gas effluent. Detection can be accomplished by a PID detector such as for example detector 151 as shown in FIG. 1A as part of system 100, which can be for example a photo ionization detector (PID).

Figure 15:
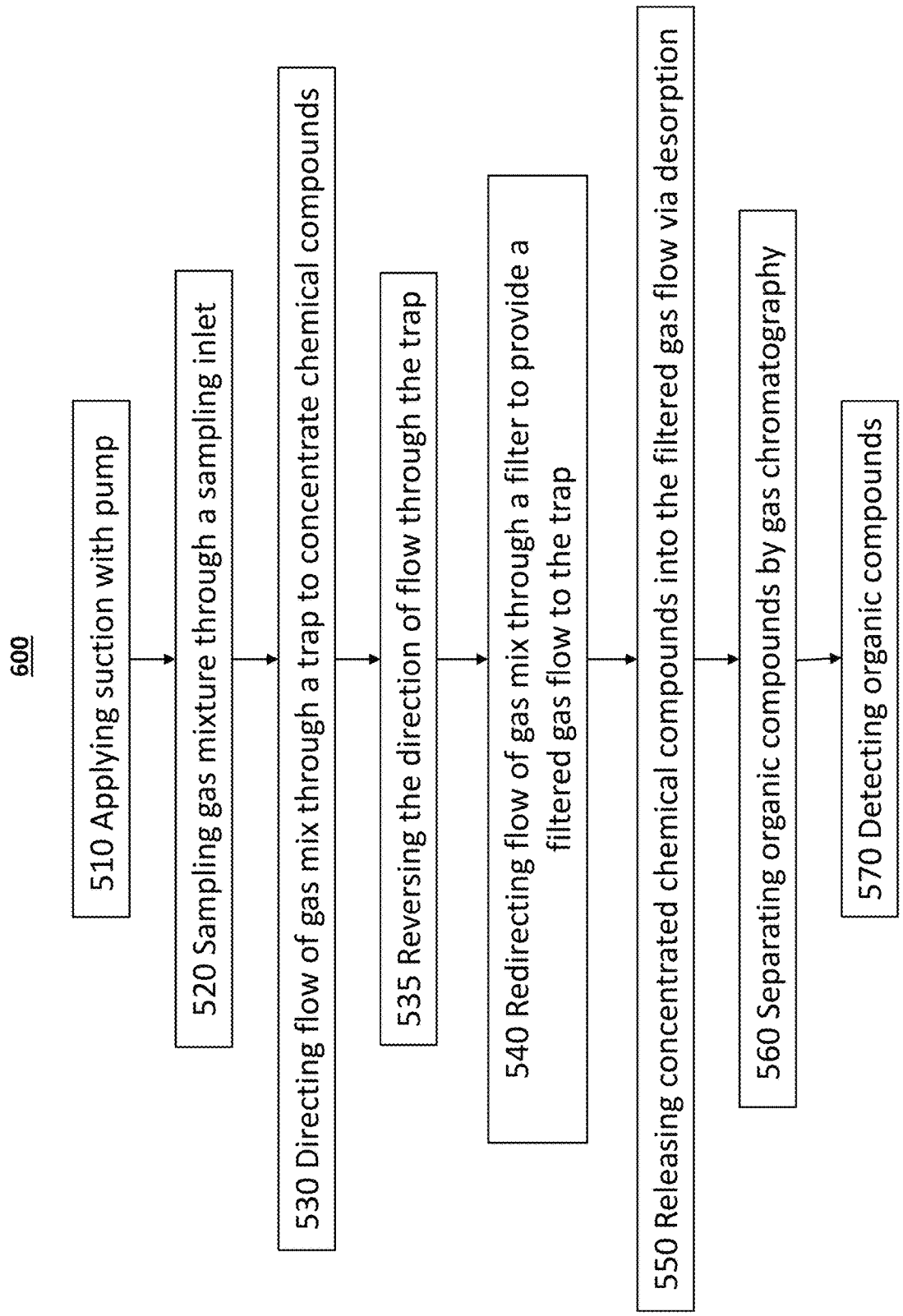
FIG. 15 is a flow chart of a gas chromatography method for identifying and quantifying organic compounds in gas environments according to one embodiment of the invention.

Referring to FIG. 15, an alternate embodiment 600 of the method of the invention is shown. Method 600 is similar to method 500, but includes the step 535 of reversing the direction of flow through the trap after directing the flow of gas through a trap, but before redirecting the flow through a filter to provide filtered gas flow to the trap.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compositions of the present invention and practice the claimed methods. The following working examples therefore, specifically point out the preferred embodiments of the present invention, and are not to be construed as limiting in any way the remainder of the disclosure.

Example 1

Figure 11A:
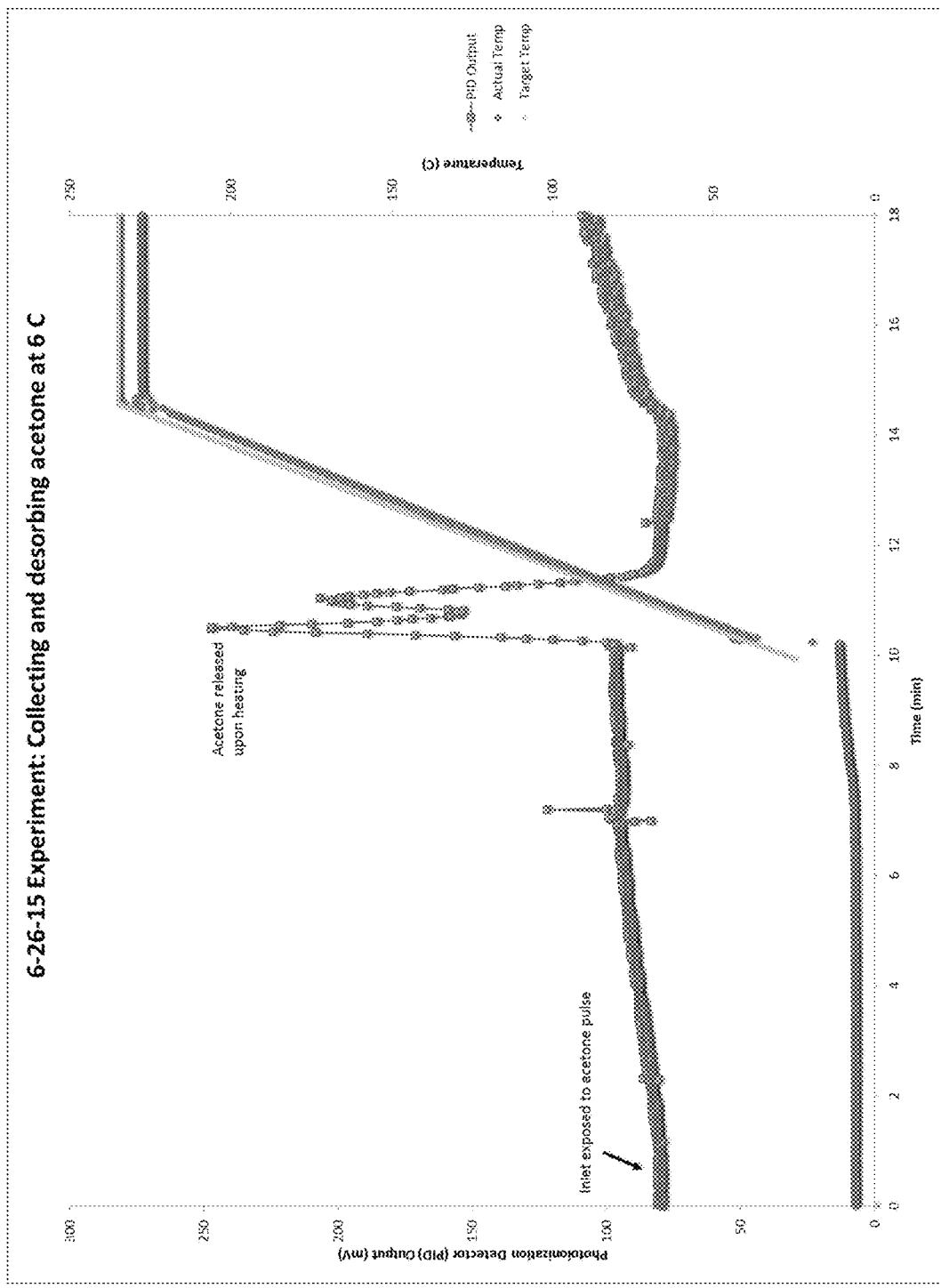
FIG. 11A is a chart depicting the results of an experiment for cooled sample collection and desorption of a high volatility analyte using the apparatus according to one embodiment of the invention.

As depicted in FIG. 11A a system of the invention was used to detect acetone in an air/acetone mixture. First, a sample inlet was exposed to a pulse of acetone in air. The system was allowed about ten minutes to trap and concentrate acetone in a cooled bed of adsorbent material. After about ten minutes, the adsorbent bed heaters were powered to provide a temperature gradient increase of about 60° C./minute. After about 30 seconds a peak was detected in the output of the photo ionization detector.

Example 2

Figure 11B:
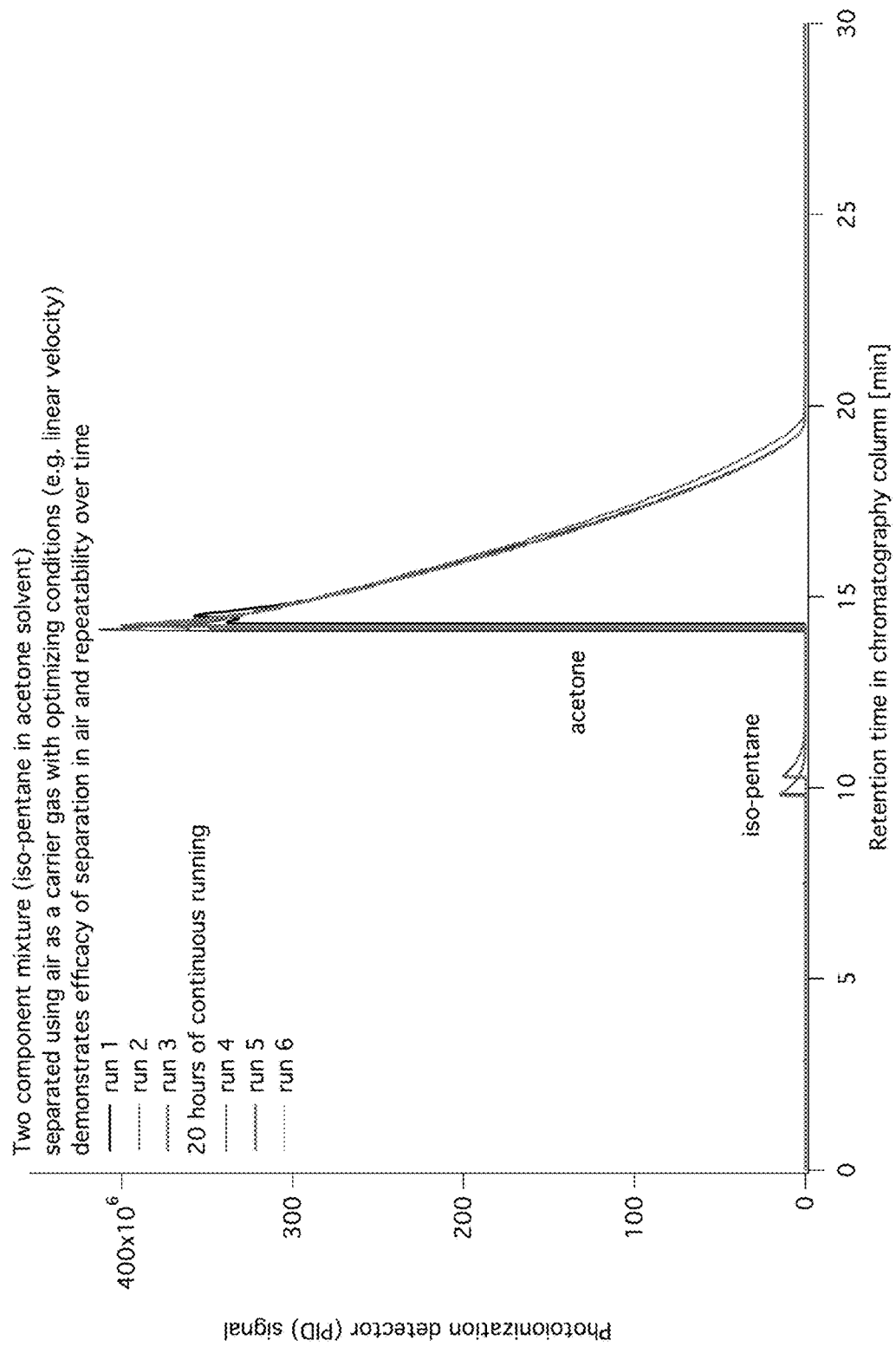
FIG. 11B is a chart depicting the results of an experiment for separating a two component mixture with air as carrier gas using an apparatus according to one embodiment of the invention.

As depicted in FIG. 11B a system of the invention was used to separate and detect iso-pentane and acetone using air as carrier gas in a gas chromatography method. Six separate runs of the separation method, including three runs performed after twenty hours of continuous running, demonstrated the high efficacy of separation and repeatability over time.

Example 3

Figure 12A:
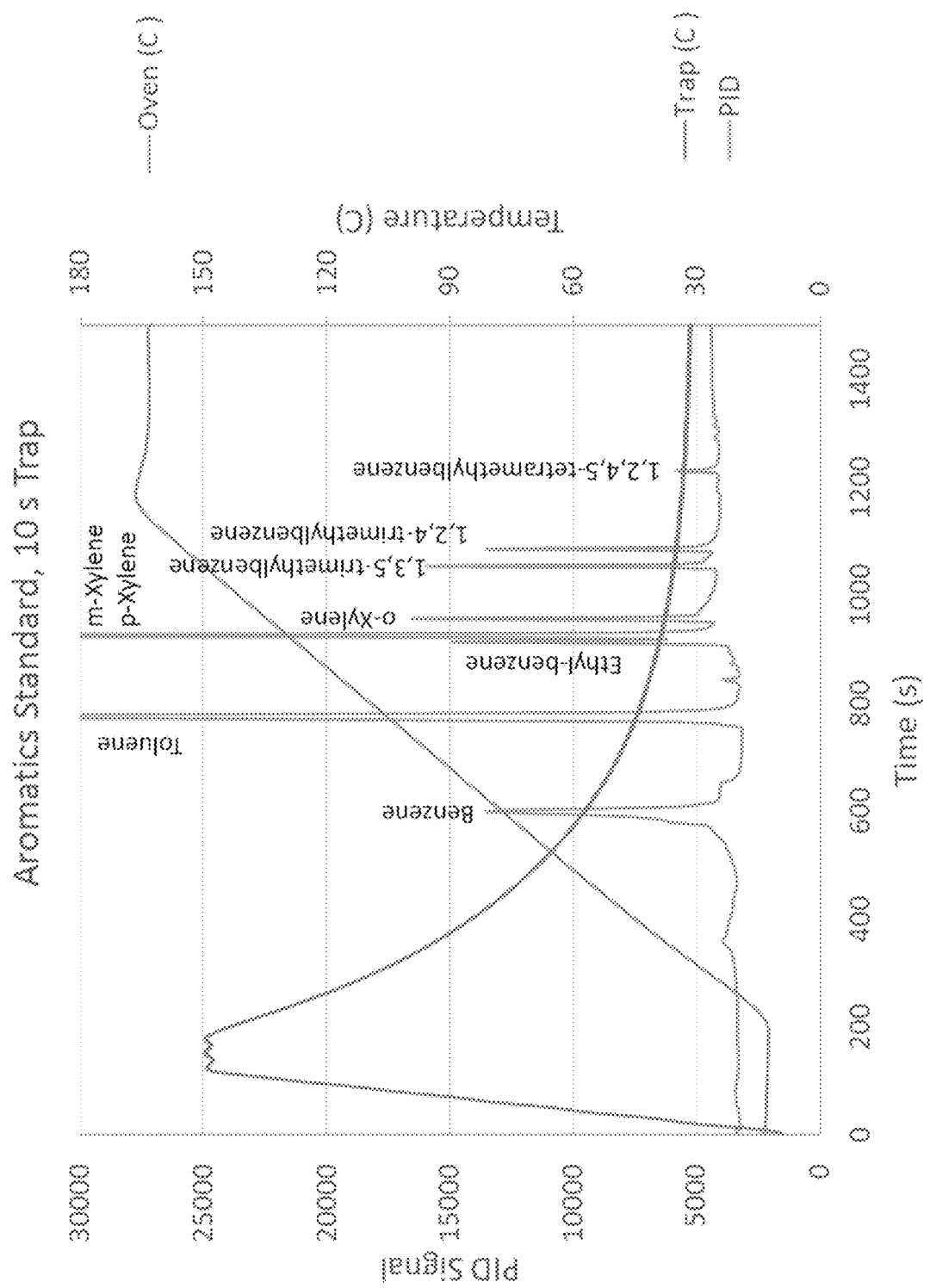
FIG. 12A is a chart depicting the results of an experiment testing the "trap-and-run" mode of one embodiment of the invention.

As depicted in FIG. 12A, a system of the invention was used in trap mode and run mode for the complete autonomous device without any external pressure or vacuum and no additional equipment. The figure shows a "chromatogram" with the PID sensor output, trap temperature, and oven temperatures along the Y axis and run-time along the X axis. An analytical standard mixture of single-ring aromatic compounds was sampled from the gas phase, trapped, retained, and then injected onto the column where it was separated under vacuum over the automatic temperature program, and then measured on the PID. The compounds shown include the common and challenging BTEX compounds that are of high interest in the scientific, regulatory, and commercial community. Specific analytes measured and labeled are benzene, toluene, ethyl-benzene, m-xylene with p-xylene, o-xylene, 1,2,4-Trimethylbenzene, 1,3,5-Trimethylbenzene, and 1,2,4,5-Tetramethylbenzene.

Example 4

Figure 12B:
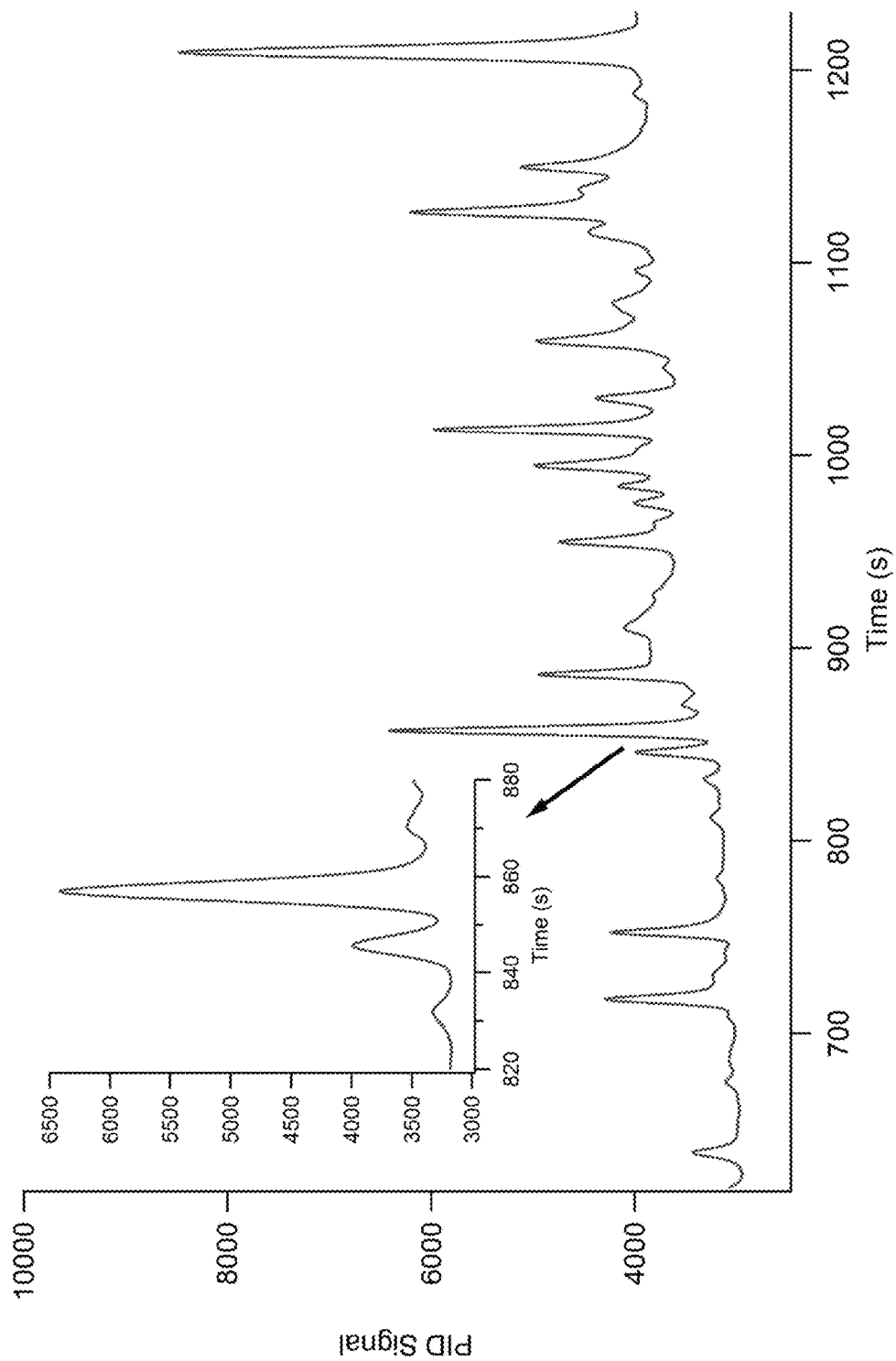
FIG. 12B is a chart depicting the results of an experimental chromatogram of an ambient air sample.

As depicted in FIG. 12B, a chromatogram and a focused section of a chromatogram are shown, depicting the results of a twenty minute trap and desorption of an indoor air sample, collected using only the device itself as described in FIG. 12A. The peaks shown are all volatile organic compounds present in the room at trace concentrations (e.g. ppb or ppt). The graph and its subplot are zoomed in on a portion of the chromatogram to demonstrate the quantity of resolved peaks, the abundance of narrow peaks, excellent peak shape, and resolution between peaks.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A system for analyzing a gas mixture, comprising:
   a filter;
   a flow constrictor;
   a trap;
   a chromatographic column;
   a detector; and
   a pump,
   wherein the trap and the pump are fluidly connected to form a first gas flow path with the pump positioned downstream of the trap,
   wherein the filter, the flow constrictor, the trap, the chromatographic column, the detector, and the pump, are fluidly connected to form a second gas flow path, with the pump positioned downstream of the filter, the trap, the chromatographic column, and the detector, and the flow constrictor is positioned upstream of the trap, the chromatographic column, the detector, and the pump; and
   wherein the flow constrictor is positioned only in the second gas flow path.

2. The system of claim 1, wherein the detector and the pump are fluidly connected to form a third gas flow path.

3. The system of claim 1, wherein the chromatographic column is selected from the group consisting of a gas-solid adsorption chromatographic column, and a gas-liquid gas chromatography column.

4. The system of claim 1, wherein the trap further comprises an adsorbent material.

5. The system of claim 1, wherein the filter is an activated charcoal filter.

6. The system of claim 1, wherein the detector is selected from the group consisting of a photo ionization detector, a mass spectrometer, a spectrophotometer, and a thermal conductivity detector.

7. The system of claim 1, wherein the detector is a photo ionization detector.

8. The system of claim 1, wherein the pump provides negative pressure.

9. The system of claim 1, further comprising a housing.

10. The system of claim 9, wherein the housing is no larger than 216 cubic inch.

11. The system of claim 1, wherein the system is capable of detecting chemical compounds with a sensitivity of parts-per-trillion.

12. A system for analyzing a gas mixture, comprising:
    a filter;
    a flow constrictor;
    a trap;
    a chromatographic column;
    a detector; and
    a pump,
    wherein the trap and the pump are fluidly connected to form a first gas flow path with the pump positioned downstream of the trap,
    wherein the filter, the flow constrictor, the trap, the chromatographic column, the detector, and the pump, are fluidly connected to form a second gas flow path, with the pump positioned downstream of the filter, the flow constrictor, the trap, the chromatographic column, and the detector, and the flow constrictor is positioned downstream of the filter and upstream of the trap, the chromatographic column, the detector, and the pump.

13. A system for analyzing a gas mixture, comprising:
a first gas flow path having a trap and a downstream pump configured to direct a first flow of gas; and
a second gas flow path having the trap, a flow constrictor upstream of the trap, a chromatographic column, a detector, and the downstream pump configured to direct a second flow of gas;
wherein the second flow of gas exiting the flow constrictor in the second gas flow path enters the trap in a direction opposite the first flow of gas.

* * * * *